(12) United States Patent
Jafarkhani et al.

(10) Patent No.: US 11,990,224 B2
(45) Date of Patent: May 21, 2024

(54) SYNTHETICALLY GENERATING MEDICAL IMAGES USING DEEP CONVOLUTIONAL GENERATIVE ADVERSARIAL NETWORKS

(71) Applicant: THE REGENTS OF THE UNIVERSITY OF CALIFORNIA, Oakland, CA (US)

(72) Inventors: Hamid Jafarkhani, Irvine, CA (US); Saeed Karimi-Bidhendi, Irvine, CA (US); Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 519 days.

(21) Appl. No.: 17/214,442

(22) Filed: Mar. 26, 2021

(65) Prior Publication Data

US 2021/0312242 A1    Oct. 7, 2021

Related U.S. Application Data

(60) Provisional application No. 63/000,401, filed on Mar. 26, 2020.

(51) Int. Cl.
  *G06T 7/143* (2017.01)
  *G06F 18/21* (2023.01)
  (Continued)

(52) U.S. Cl.
  CPC ......... *G16H 30/40* (2018.01); *G06F 18/2148* (2023.01); *G06F 18/2185* (2023.01);
  (Continued)

(58) Field of Classification Search
  CPC ................. G16H 30/40; G06T 7/0012; G06T 2207/10088; G06T 2207/10081;
  (Continued)

(56) References Cited

U.S. PATENT DOCUMENTS 11,398,026 B2 *   7/2022   Hooper ................. G06N 3/088
11,645,833 B2 *   5/2023   Madani ............... G06F 18/2155
                                                          382/132

(Continued)

FOREIGN PATENT DOCUMENTS

CN        110807762  A  *  2/2020  ........... G06N 3/0454

OTHER PUBLICATIONS

Creswell et al. "Generative adversarial networks: An overview." IEEE signal processing magazine 35.1 (2018): 53-65 (Year: 2018).*
(Continued)

*Primary Examiner* — Sumati Lefkowitz
*Assistant Examiner* — Michael Adam Shariff
(74) *Attorney, Agent, or Firm* — Perkins Coie LLP

(57) ABSTRACT

Methods, devices, and systems that are related to facilitating an automated, fast and accurate model for cardiac image segmentation, particularly for image data of children with complex congenital heart disease are disclosed. In one example aspect, a generative adversarial network is disclosed. The generative adversarial network includes a generator configured to generate synthetic imaging samples associated with a cardiovascular system, and a discriminator configured to receive the synthetic imaging samples from the generator and determine probabilities indicating likelihood of the synthetic imaging samples corresponding to real cardiovascular imaging sample. The discriminator is further configured to provide the probabilities determined by the discriminator to the generator and the discriminator to allow the parameters of the generator and the parameters of the discriminator to be adjusted iteratively until an equilibrium between the generator and the discriminator is established.

20 Claims, 20 Drawing Sheets

(51) Int. Cl.
| | |
|---|---|
| *G06F 18/214* | (2023.01) |
| *G06N 3/08* | (2023.01) |
| *G06N 7/01* | (2023.01) |
| *G06T 7/00* | (2017.01) |
| *G06V 10/82* | (2022.01) |
| *G16H 30/40* | (2018.01) |

(52) U.S. Cl.
CPC ........... *G06F 18/2193* (2023.01); *G06N 3/08* (2013.01); *G06N 7/01* (2023.01); *G06T 7/0012* (2013.01); *G06T 7/143* (2017.01); *G06V 10/82* (2022.01); *G06T 2207/10088* (2013.01); *G06T 2207/20084* (2013.01); *G06T 2207/30048* (2013.01); *G06V 2201/031* (2022.01)

(58) Field of Classification Search
CPC ....... G06T 2207/30004; G06T 2211/40; G06T 7/143; G06T 7/11; G06T 2207/20084; G06T 2207/20081; G06T 2211/441; G06T 2207/30048; G06V 2201/03; G06V 2201/031; G06V 10/82; G06F 18/214; G06F 18/2148; G06F 18/2185; G06F 18/2193; G06N 7/01; G06N 3/08; G06N 20/00; G06N 3/045; G06N 3/0895; G06N 3/09; G06N 3/091; G06N 3/092; G06N 3/094; G06N 3/096; G06N 3/098; G06N 3/0985; G06N 3/0475; G06N 3/04; G06N 3/047; G06N 3/088; A61B 5/7267
See application file for complete search history.

(56) References Cited

U.S. PATENT DOCUMENTS

| | | | | |
|---|---|---|---|---|
| 2021/0249142 A1* | 8/2021 | Lau | ........................ | G06N 3/047 |
| 2021/0342703 A1* | 11/2021 | Wei | ........................ | G06N 3/047 |

OTHER PUBLICATIONS

Arafati et al. "Artificial intelligence in pediatric and adult congenital cardiac MRI: an unmet clinical need"; Cardiovascular diagnosis and therapy 9; Suppl 2 (2019): S310 (Year: 2019).*

Arafati, A., Hu, P., Finn, J.P., Rickers, C., Cheng, A.L., Jafarkhani, H., Kheradvar, A.: Artificial intelligence in pediatric and adult congenital cardiac mri: an unmet clinical need. Cardiovascular diagnosis and therapy 9(Suppl 2), 310 (2019).

Avendi, M., Kheradvar, A., Jafarkhani, H.: A combined deep-learning and deformable-model approach to fully automatic segmentation of the left ventricle in cardiac mri. Medical image analysis 30, 108-119 (2016).

Avendi, M.R., Kheradvar, A., Jafarkhani, H.: Automatic segmentation of the right ventricle from cardiac mri using a learning-based approach. Magnetic resonance in medicine 78(6), 2439-2448 (2017).

Backhaus, S.J., et al.: Fully automated quantification of biventricular volumes and function in cardiovascular magnetic resonance: applicability to clinical routine settings. Journal of Cardiovascular Magnetic Resonance 21(1), 24 (2019).

Bai, W., et al.: Automated cardiovascular magnetic resonance image analysis with fully convolutional networks. Journal of Cardiovascular Magnetic Resonance 20(1), 65 (2018).

Best, K.E., Rankin, J.: Long-term survival of individuals born with congenital heart disease: a systematic review and meta-analysis. Journal of the American Heart Association 5(6), 002846 (2016).

Dreijer, J.F., Herbst, B.M., Du Preez, J.A .: Left ventricular segmentation from mri datasets with edge modelling conditional random fields. BMC medical imaging 13(1), 24 (2013).

Glorot, X., Bengio, Y.: Understanding the difficulty of training deep feedforward neural networks. In: Proceedings of the Thirteenth International Conference on Artificial Intelligence and Statistics, pp. 249-256 (2010).

Heusel, M., Ramsauer, H., Unterthiner, T., Nessler, B., Hochreiter, S.: Gans trained by a two time-scale update rule converge to a local nash equilibrium. In: Advances in Neural Information Processing Systems, pp. 6626-6637 (2017).

Kazeminia, S., Baur, C., Kuijper, A., van Ginneken, B., Navab, N., Albarqouni, S., Mukhopadhyay, A.: Gans for medical image analysis. arXiv preprint arXiv:1809.06222 (2018).

Kingma, D.P., Ba, J.: Adam: A method for stochastic optimization. arXiv preprint arXiv:1412.6980 (2014).

Krizhevsky, A., Sutskever, I., Hinton, G.E.: Imagenet classification with deep convolutional neural networks. In: Advances in Neural Information Processing Systems, pp. 1097-1105 (2012).

Lima, J.A., Desai, M.Y.: Cardiovascular magnetic resonance imaging: current and emerging applications. Journal of the American College of Cardiology 44(6), 1164-1171 (2004).

Litjens, G., Kooi, T., Bejnordi, B.E., Setio, A.A.A., Ciompi, F., Ghafoorian, M., Van Der Laak, J.A., Van Ginneken, B., S'anchez, C.I.: A survey on deep learning in medical image analysis. Medical image analysis 42, 60-88 (2017).

Long, J., Shelhamer, E., Darrell, T.: Fully convolutional networks for semantic segmentation. In: Proceedings of the IEEE Conference on Computer Vision and Pattern Recognition, pp. 3431-3440 (2015).

Nesterov, Y.: A method for unconstrained convex minimization problem with the rate of convergence o $(1/k^\wedge 2)$. In: Doklady An Ussr, vol. 269, pp. 543-547 (1983).

Oster, M.E., Lee, K.A., Honein, M.A., Riehle-Colarusso, T., Shin, M., Correa, A.: Temporal trends in survival among infants with critical congenital heart defects. Pediatrics 131(5), 1502-1508 (2013).

Petersen, S.E., et al.: Imaging in population science: cardiovascular magnetic resonance in 100,000 participants of uk biobank-rationale, challenges and approaches. Journal of Cardiovascular Magnetic Resonance 15(1), 46 (2013).

Petersen, S.E., et al.: Uk biobank's cardiovascular magnetic resonance protocol. Journal of cardiovascular magnetic resonance 18(1), 8 (2015).

Petitjean, C., Dacher, J.- N.: A review of segmentation methods in short axis cardiac mr images. Medical image analysis 15(2), 169-184 (2011).

Petitjean, C., Zuluaga, M.A., Bai, W., Dacher, J.-N., Grosgeorge, D., Caudron, J., Ruan, S., Ayed, I.B., Cardoso, M.J., Chen, H.-C., et al.: Right ventricle segmentation from cardiac mri: a collation study. Medical image analysis 19(1), 187-202 (2015).

Queiros, S., Barbosa, D., Heyde, B., Morais, P., Vilac a, J.L., Friboulet, D., Bernard, O., D'hooge, J.: Fast automatic myocardial segmentation in 4d cine cmr datasets. Medical image analysis 18(7), 1115-1131 (2014).

Radford, A., Metz, L., Chintala, S.: Unsupervised representation learning with deep convolutional generative adversarial networks. arXiv preprint arXiv:1511.06434 (2015).

Roth, H.R., Lu, L., Liu, J., Yao, J., Seff, A., Cherry, K., Kim, L., Summers, R.M.: Improving computer-aided detection using convolutional neural networks and random view aggregation. IEEE transactions on medical imaging 35(5), 1170-1181 (2015).

Salimans, T., Goodfellow, I., Zaremba, W., Cheung, V., Radford, A., Chen, X.: Improved techniques for training gans. In: Advances in Neural Information Processing Systems, pp. 2234-2242 (2016).

Szegedy, C., Liu, W., Jia, Y., Sermanet, P., Reed, S., Anguelov, D., Erhan, D., Vanhoucke, V., Rabinovich, A.: Going deeper with convolutions. In: Proceedings of the IEEE Conference on Computer Vision and Pattern Recognition, pp. 1-9 (2015).

Tavakoli, V., Amini, A.A.: A survey of shaped-based registration and segmentation techniques for cardiac images. Computer Vision and Image Understanding 117(9), 966-989 (2013).

The 2015 Kaggle Second Annual Data Science Bowl. www.kaggle.com/c/second-annual-data-science-bowl (2015).

Tran, P.V.: A fully convolutional neural network for cardiac segmentation in short-axis mri. arXiv preprint arXiv:1604.00494 (2016).

Yu, L., Yang, X., Qin, J., Heng, P.-A.: 3d fractalnet: dense volumetric segmentation for cardiovascular mri volumes. In: Reconstruction, Segmentation, and Analysis of Medical Images, pp. 103-110. Springer, Cham (2016).

(56) References Cited

OTHER PUBLICATIONS

Yuan, C., et al., Contrast-enhanced high resolution mri for atherosclerotic carotid artery tissue characterization. J. of Magnetic Resonance Imaging: An Official Journal of the International Society for Magnetic Resonance in Medicine 15(1), 62-67 (2002).

* cited by examiner

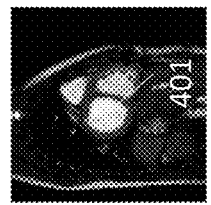
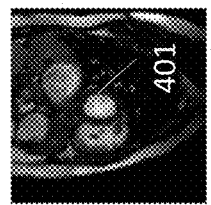
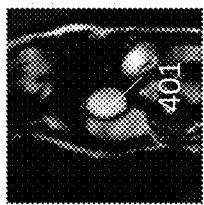
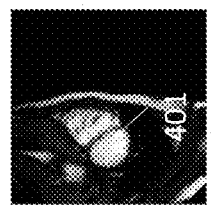
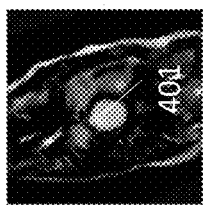
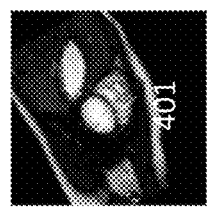
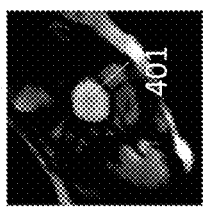
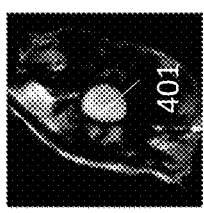
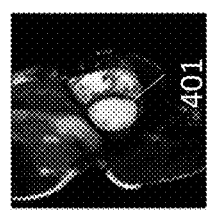
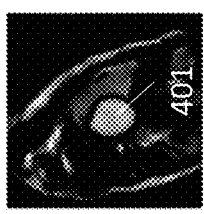
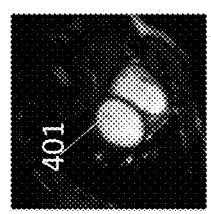
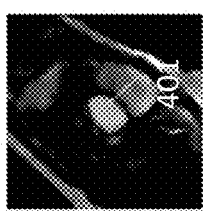
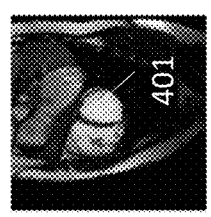
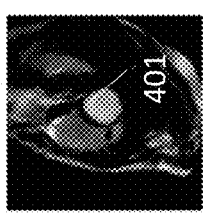
FIG. 4A
FIG. 4B

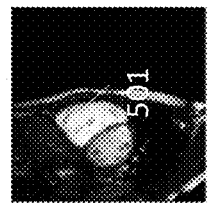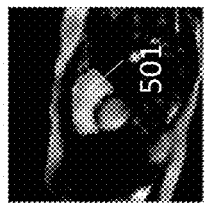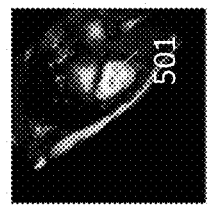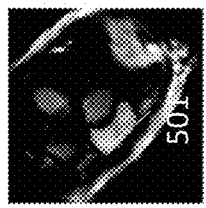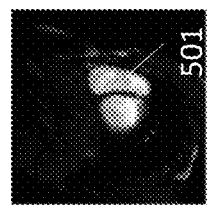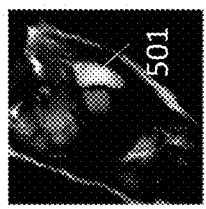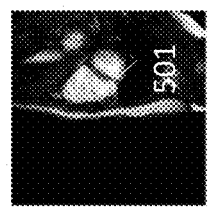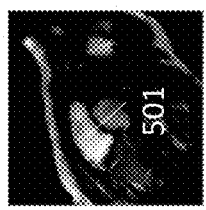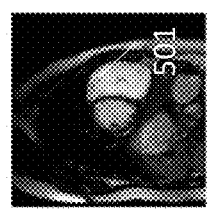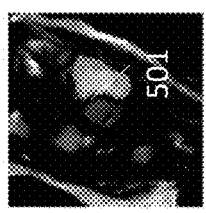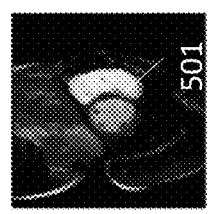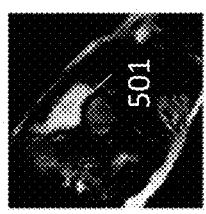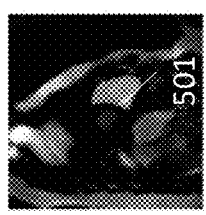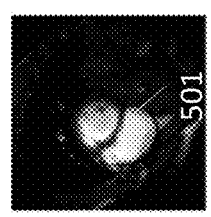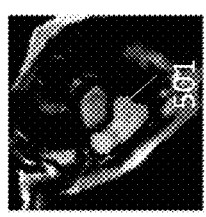
FIG. 5A
FIG. 5B

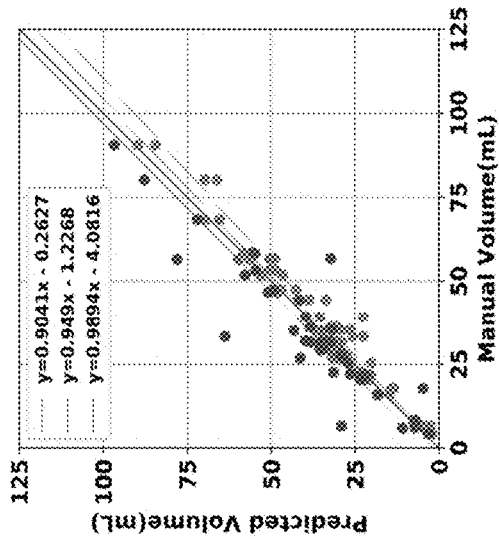
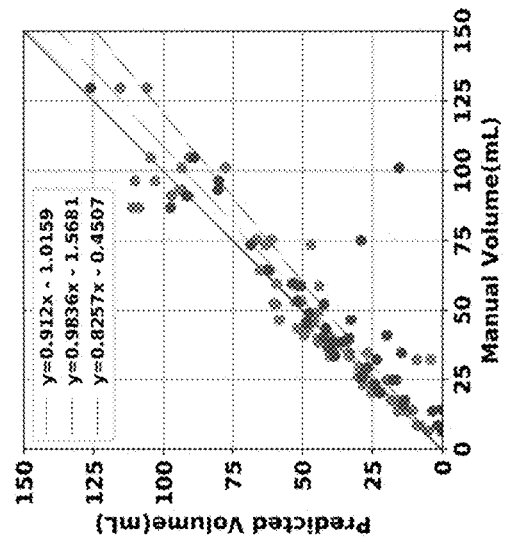
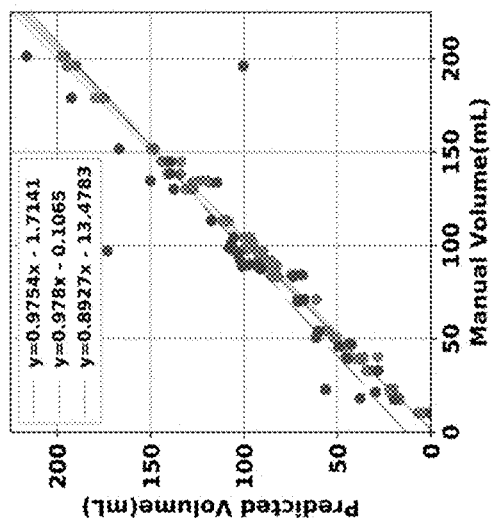
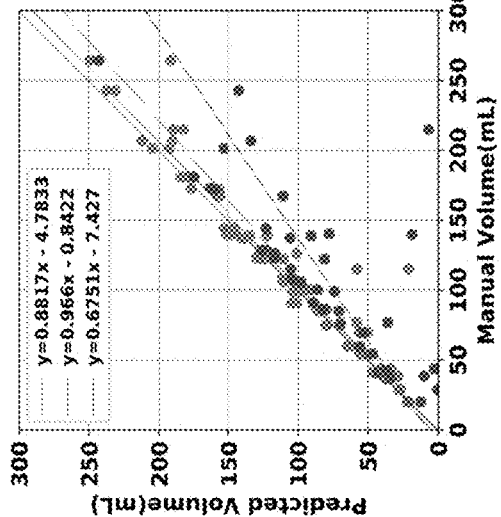
FIG. 7A
FIG. 7B
FIG. 7C
FIG. 7D

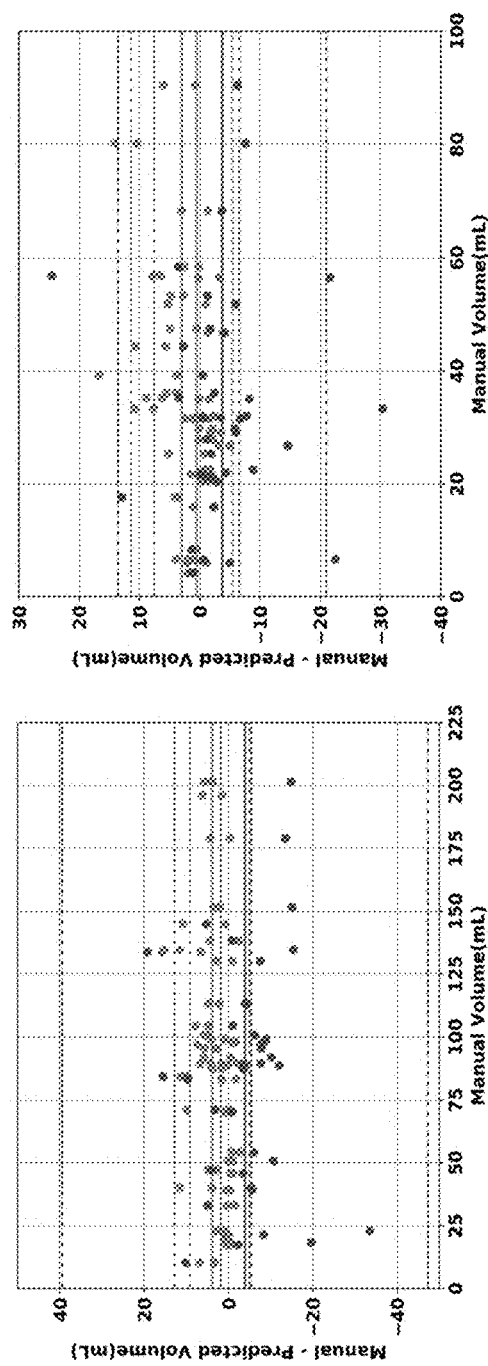
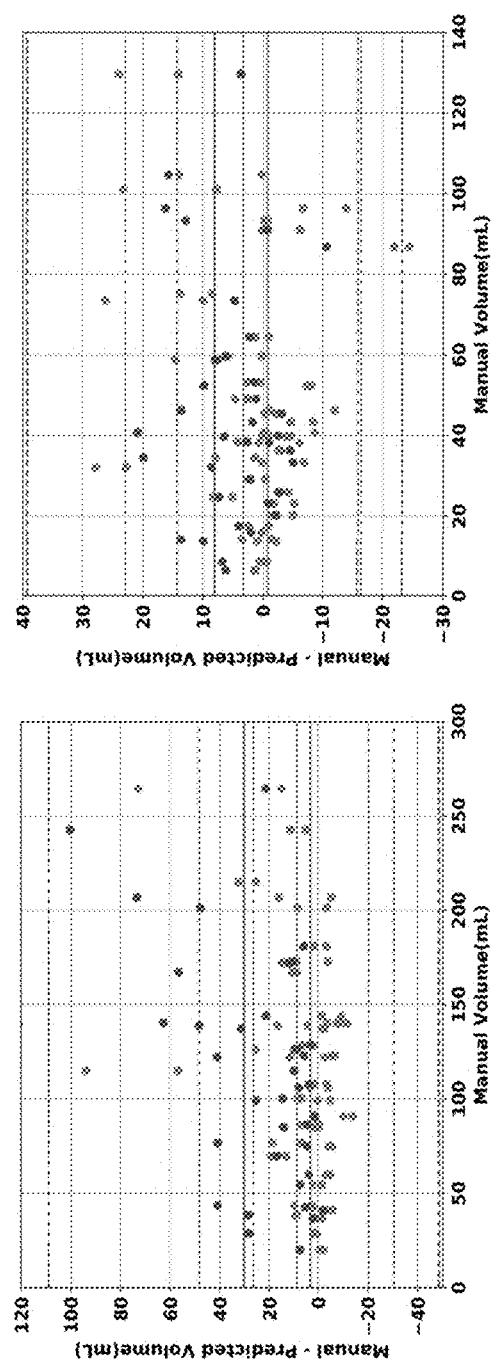
FIG. 9A
FIG. 9B
FIG. 9C
FIG. 9D

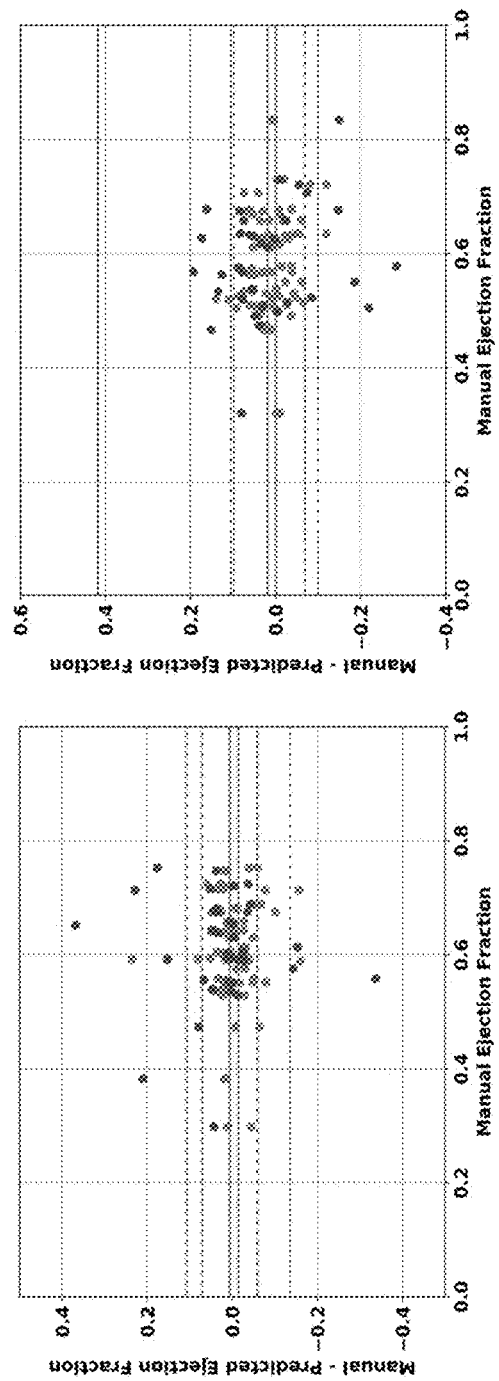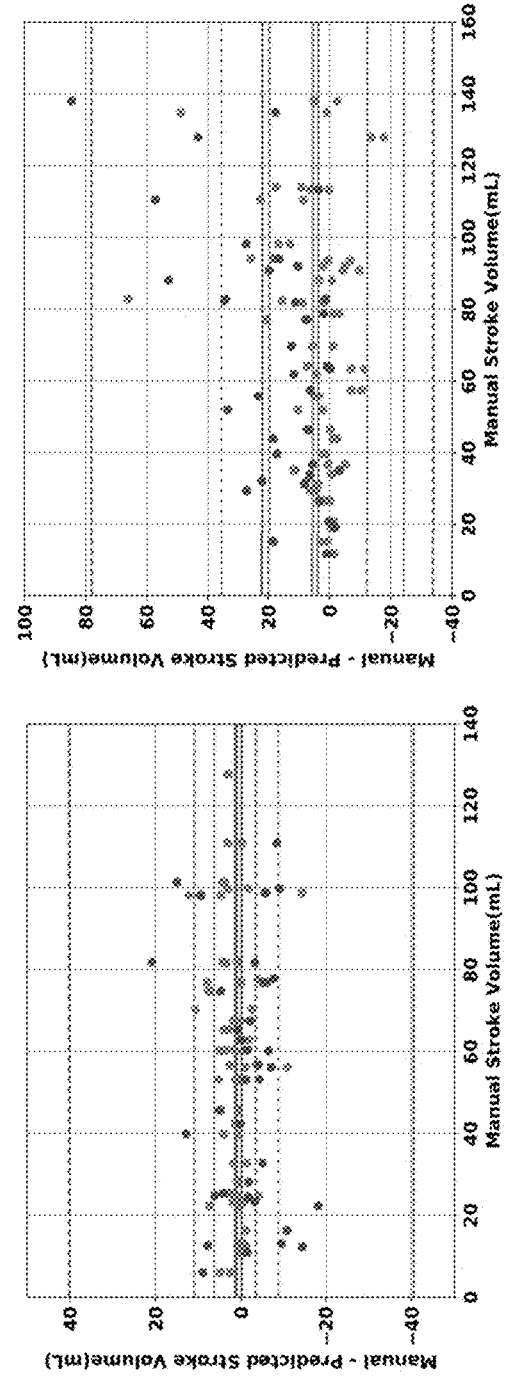
FIG. 10A
FIG. 10B
FIG. 10C
FIG. 10D

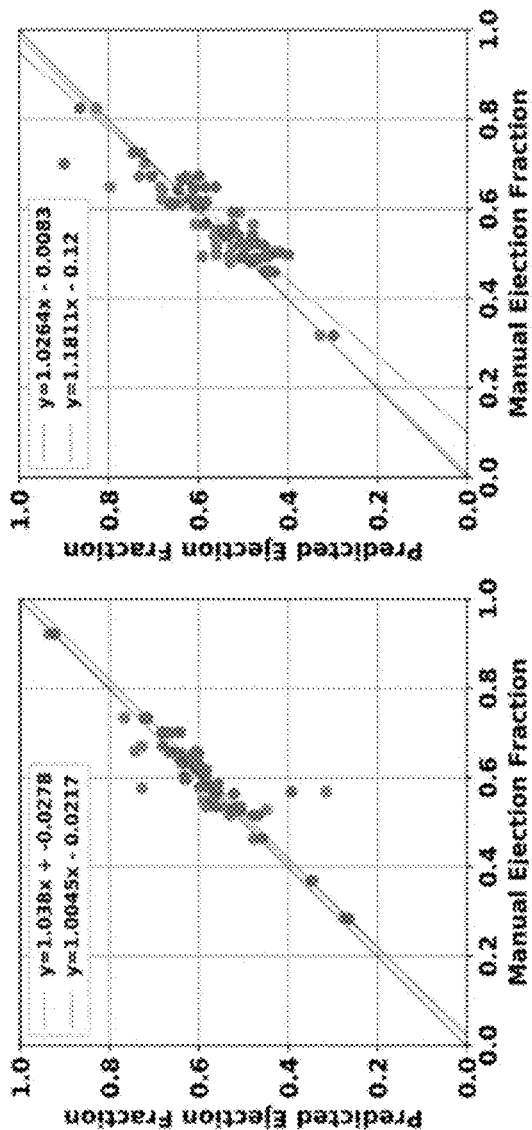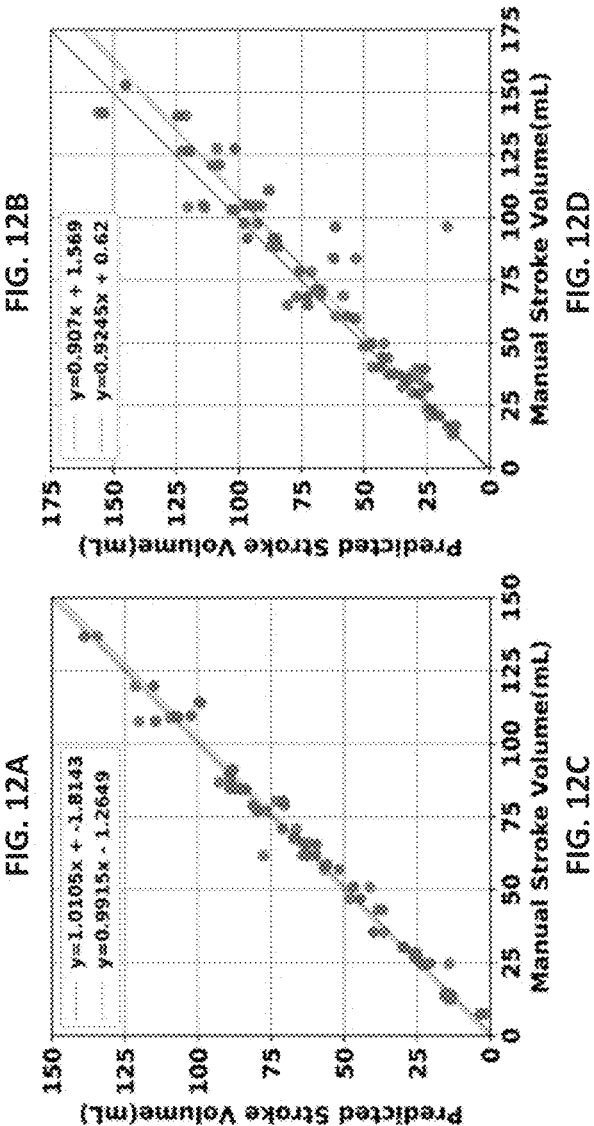
FIG. 12A  FIG. 12B  FIG. 12C  FIG. 12D

SYNTHETICALLY GENERATING MEDICAL IMAGES USING DEEP CONVOLUTIONAL GENERATIVE ADVERSARIAL NETWORKS

CROSS REFERENCE TO RELATED APPLICATIONS

This application claims priority to and benefits of U.S. Provisional Application 63/000,401, titled "Synthetically Generating Medical Images Using Deep Convolutional Generative Adversarial Networks," filed on Mar. 26, 2020. The entire disclosure of the aforementioned application is incorporated by reference as part of the disclosure of this application.

TECHNICAL FIELD

This patent document relates to medical imaging processing and analysis, and more specifically, to generation of synthetic images to facilitate fully automated segmentation of cardiac image data.

BACKGROUND

Congenital heart disease (CHD) is often caused by defects in the structure of the heart or vessels that is present at birth. It is currently estimated that 83% of newborns with CHD in the U.S. survive infancy. These patients require routine imaging follow ups. Cardiac magnetic resonance (CMR) imaging is the imaging modality of choice for assessment of cardiac function and anatomy in children with CHD since not only does CMR deliver images with high spatial and acceptable temporal resolution, but also it is non-invasive and non-ionizing. On the other hand, CMR analysis in pediatric CHD patients is among the most challenging, time-consuming and operator-intensive clinical tasks.

SUMMARY

The present document discloses techniques that can be implemented in various embodiments to generate synthetic medical images to an automated, fast and accurate model for cardiac image segmentation, particularly for image data of children with complex congenital heart disease.

In one example aspect, a generative adversarial network is disclosed. The generative adversarial network includes a generator configured to generate synthetic medical images attributed to a cardiovascular system. The generator has parameters that have been initialized according to a predetermined probability distribution. The generative adversarial network also includes a discriminator configured to receive the synthetic medical images from the generator and determine probabilities indicating likelihood of the synthetic medical images corresponding to real cardiovascular images acquired from an individual. The discriminator has parameters that have been initialized according to the predetermined probability distribution. The discriminator is further configured to provide the probabilities determined by the discriminator to the generator and the discriminator to allow the parameters of the generator and the parameters of the discriminator to be iteratively adjusted until an equilibrium between the generator and the discriminator is established.

In another example aspect, a computer-implemented method for generating synthetic image data associated with a cardiovascular system is disclosed. The method includes initializing parameters of a generator and a discriminator of a generative adversarial network according to a predetermined probability distribution. The method includes generating, by the generator, synthetic medical images attributed to a cardiovascular system, and determining, by the discriminator, probabilities indicating likelihood of the synthetic medical images corresponding to real cardiovascular images acquired from an individual. The method also includes adjusting the parameters of the generator and the parameters of the discriminator based on the probabilities determined by the discriminator in an iterative process until an equilibrium between the generator and the discriminator is established. In the iterative process, the parameters of the generator remain unchanged when the parameters of the discriminator are adjusted, and the parameters of the discriminator remain unchanged when the parameters of the generator are adjusted.

In yet another example aspect, a non-transitory computer readable medium is disclosed. The computer readable medium has code stored thereon, wherein the code, when executed by a processor, causes the processor to implement a method that includes initializing parameters of a generator and a discriminator of a generative adversarial network according to a predetermined probability distribution, generating synthetic medical images attributed the cardiovascular system using the generator, and determining, by the discriminator, probabilities indicating likelihood of the synthetic medical images corresponding to real cardiovascular images acquired from an individual. The method also includes adjusting the parameters of the generator and the parameters of the discriminator based on the probabilities determined by the discriminator in an iterative process until an equilibrium between the generator and the discriminator is established. In the iterative process, the parameters of the generator remain unchanged when the parameters of the discriminator are adjusted and the parameters of the discriminator remain unchanged when the parameters of the generator are adjusted.

BRIEF DESCRIPTION OF THE DRAWINGS

FIG. 4A illustrates real sample segmented images for left ventricle.

FIG. 4B illustrates synthetic sample segmented images for left ventricle.

FIG. 5A illustrates real sample segmented images for right ventricle.

FIG. 5B illustrates synthetic sample segmented images for right ventricle.

FIG. 7A illustrates an example correlation plot for nearest-neighbor down-sampling.

FIG. 7B illustrates another example correlation plot for nearest-neighbor down-sampling.

FIG. 7C illustrates another example correlation plot for nearest-neighbor down-sampling.

FIG. 7D illustrates yet another example correlation plot for nearest-neighbor down-sampling.

FIG. 9A illustrates an example Bland-Altman plot for nearest-neighbor down-sampling.

FIG. 9B illustrates another example Bland-Altman plot for nearest-neighbor down-sampling.

FIG. 9C illustrates another example Bland-Altman plot for nearest-neighbor down-sampling.

FIG. 9D illustrates yet another example Bland-Altman plot for nearest-neighbor down-sampling.

FIG. 10A illustrates an example Bland-Altman plot for nearest-neighbor down-sampling.

FIG. 10B illustrates another example Bland-Altman plot for nearest-neighbor down-sampling.

FIG. 10C illustrates another example Bland-Altman plot for nearest-neighbor down-sampling.

FIG. 10D illustrates yet another example Bland-Altman plot for nearest-neighbor down-sampling.

FIG. 12A illustrates an example correlation plot for bi-cubical down-sampling.

FIG. 12B illustrates another example correlation plot for bi-cubical down-sampling.

FIG. 12C illustrates another example correlation plot for bi-cubical down-sampling.

FIG. 12D illustrates yet another example correlation plot for bi-cubical down-sampling.

DETAILED DESCRIPTION

Figure 1A:
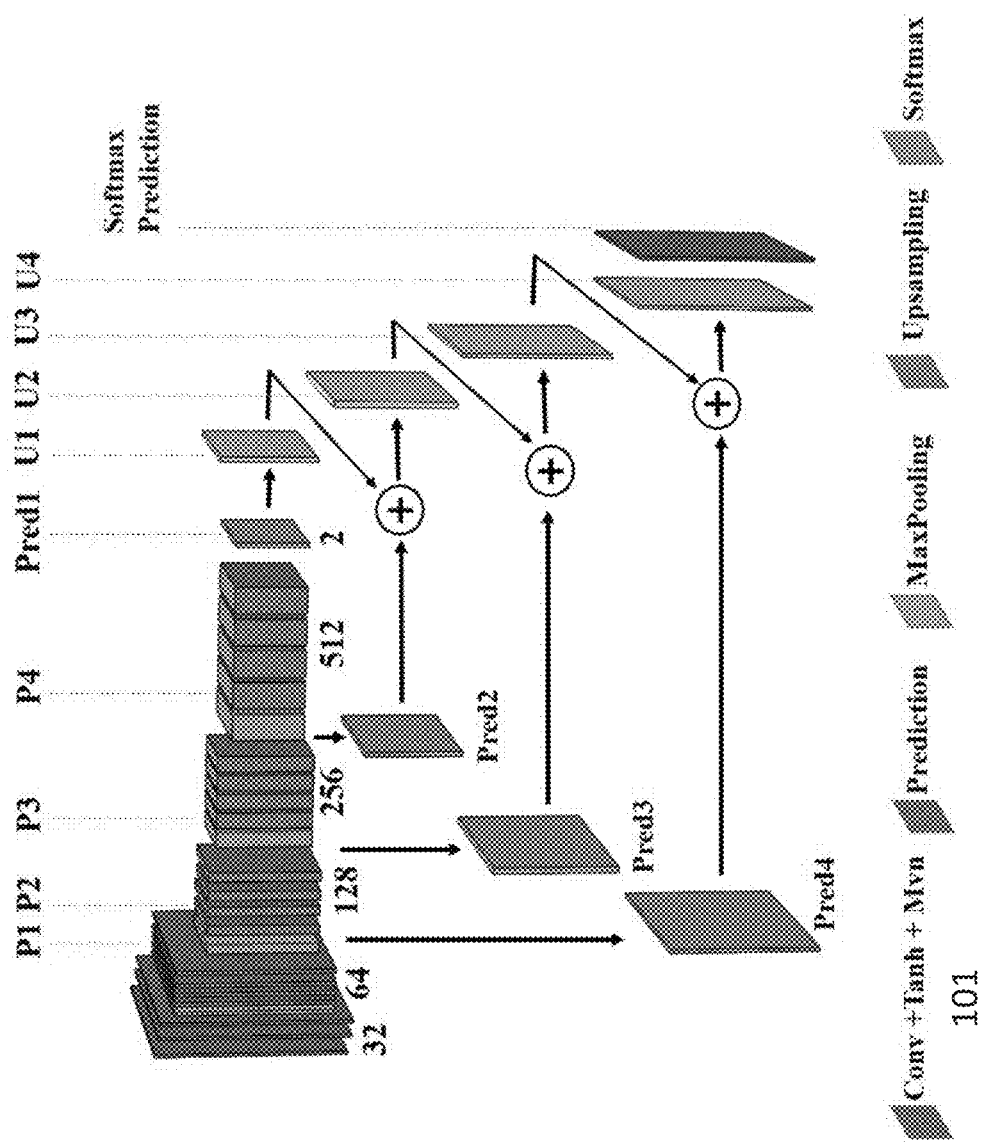
FIG. 1A illustrates an example fully convolutional network (FCN) architecture in accordance with one or more embodiments of the present technology.

With the development of artificial intelligence (AI), neural network based deep-learning has been used for automatic segmentation of CMR images. While the current AI-based methods have shown success in delineating the adult heart disease, they are not yet reliable for segmenting the CMR images of CHD patients, and particularly in children. The foremost basis for this shortcoming is the anatomical heterogeneity and lack of large CMR databases that includes data from a diverse group of CHD subjects. A major limitation of the existing learning methods is the use of homogeneous datasets where the majority of the CMR data are from healthy adult subjects or closely mimicking healthy hearts, e.g., the Second Annual Data Science Bowl and UK CMR Biobank, among others.

Training neural networks requires a large set of data that does not currently exist for complex CHD subjects. Another limitation is overfitting, especially over training, to image patterns in a specific dataset that includes images from the same scanner model/vendor. Dealing with limited data is a major challenge in designing effective neural networks for pediatric CMR, particularly for CHD subjects, and necessitates innovative approaches.

Among the learning-based algorithms, supervised deep-learning is currently considered the state-of-the-art for CMR segmentation. Nevertheless, deep-learning methods' major limitations are their dependence on the number of manually-annotated training data. Small datasets can incur a large bias, which makes these methods ineffective and unreliable when the heart shape is outside the learning set, as frequently observed in CHD subjects.

This patent document discloses various techniques that, that among other features and benefits, can be implemented to mitigate the need for large datasets of manually-annotated CHD data. In some embodiments, a Deep Convolutional Generative Adversarial Network (DCGAN) is employed to generate synthetically segmented CMR images and further enrich the training data beyond the classical affine transformations. The disclosed DCGAN implantations enable successful and accurate segmentation of CMR images associated with complex CHD subjects.

Example Dataset

In some embodiments, a dataset including 64 CMR studies from pediatric patients with an age range of 2 to 18 is used. The CMR dataset includes Tetralogy of Fallot (TOF; n=20), Double Outlet Right Ventricle (DORV; n=9), Transposition of the Great Arteries (TGA; n=9), Cardiomyopathy (n=8), Coronary Artery Anomaly (Coronary artery anomaly (CAA); n=9), Pulmonary Stenosis or Atresia (n=4), Truncus Arteriosus (n=3), and Aortic Arch Anomaly (n=2). Table 1 shows the characteristics of the cohort (Volumes) and Table 2 shows the characteristics of the cohort (Age, Weight, Height).

TABLE 1

Characteristics of the cohort (Volumes)

| | n | Min | Max | Mean | Median |
|---|---|---|---|---|---|
| LVEDV (mL) | | | | | |
| Aortic Arch Anomaly | 2 | 87.39 | 196.09 | 141.74 | 141.74 |
| Cardiomyopathy | 8 | 82.55 | 179.02 | 114.37 | 93.66 |
| Coronary Artery Disease | 9 | 21.43 | 123.24 | 79.72 | 89.55 |
| DORV | 9 | 10.23 | 126.6 | 44.8 | 40.05 |
| Pulmonary Stenosis/Atresia | 4 | 88.74 | 130.22 | 101.83 | 94.18 |
| TGA | 9 | 39.18 | 167.03 | 113.35 | 133.77 |
| TOF | 20 | 18.32 | 153.68 | 87.55 | 92.19 |
| Truncus arteriosus | 3 | 70.23 | 201.44 | 124.13 | 100.73 |
| All | 64 | 10.23 | 201.44 | 91.72 | 89.41 |
| LVESV (mL) | | | | | |
| Aortic Arch Anomaly | 2 | 22.06 | 68.3 | 45.18 | 45.18 |
| Cardiomyopathy | 8 | 15.07 | 80.2 | 41.1 | 32.5 |
| Coronary Artery Disease | 9 | 8.28 | 58.6 | 28.99 | 29.76 |
| DORV | 9 | 4.18 | 43.33 | 17.4 | 17.7 |
| Pulmonary Stenosis/Atresia | 4 | 31.56 | 53.28 | 38.25 | 34.09 |
| TGA | 9 | 15.94 | 68.86 | 45.62 | 46.71 |
| TOF | 20 | 5.95 | 69.01 | 34.21 | 33.22 |
| Truncus arteriosus | 3 | 27.88 | 90.48 | 55.28 | 47.47 |
| All | 64 | 4.18 | 90.48 | 35.16 | 31.66 |
| RVEDV (mL) | | | | | |
| Aortic Arch Anomaly | 2 | 100.34 | 215.08 | 157.71 | 157.71 |
| Cardiomyopathy | 8 | 78.94 | 180.94 | 121.31 | 114.3 |
| Coronary Artery Disease | 9 | 20.13 | 171.28 | 92.35 | 106.01 |
| DORV | 9 | 25.31 | 236.22 | 80.0 | 69.72 |
| Pulmonary Stenosis/Atresia | 4 | 126.2 | 264.54 | 176.92 | 158.48 |
| TGA | 9 | 42.58 | 179.98 | 121.33 | 138.93 |
| TOF | 20 | 28.63 | 265.7 | 137.12 | 129.67 |
| Truncus arteriosus | 3 | 99.15 | 201.42 | 147.0 | 140.43 |
| All | 64 | 20.13 | 265.7 | 122.19 | 115.43 |
| RVESV (mL) | | | | | |
| Aortic Arch Anomaly | 2 | 38.43 | 101.04 | 69.73 | 69.73 |
| Cardiomyopathy | 8 | 13.27 | 86.81 | 45.25 | 36.43 |
| Coronary Artery Disease | 9 | 8.49 | 70.26 | 34.04 | 33.57 |
| DORV | 9 | 6.37 | 112.31 | 35.91 | 34.51 |
| Pulmonary Stenosis/Atresia | 4 | 49.04 | 129.65 | 80.72 | 72.09 |
| TGA | 9 | 15.93 | 84.68 | 50.08 | 41.52 |
| TOF | 20 | 13.56 | 136.99 | 63.74 | 59.21 |
| Truncus arteriosus | 3 | 43.3 | 73.47 | 56.37 | 52.34 |
| All | 64 | 6.37 | 136.99 | 52.32 | 46.07 |

TABLE 2

Characteristics of the cohort (Age, Weight, Height)

| | n | Min | Max | Mean | Median |
|---|---|---|---|---|---|
| Age (years) | | | | | |
| Aortic Arch Anomaly | 2 | 17.9 | 18.3 | 18.1 | 18.1 |
| Cardiomyopathy | 8 | 9.4 | 17.1 | 13.6 | 13.9 |
| Coronary Artery Disease | 9 | 1.1 | 19.8 | 9.8 | 11.5 |
| DORV | 9 | 0.5 | 13.0 | 6.9 | 7.5 |
| Pulmonary Stenosis/Atresia | 4 | 8.6 | 16.5 | 12.9 | 13.2 |
| TGA | 9 | 2.7 | 18.9 | 11.2 | 11.7 |
| TOF | 20 | 0.4 | 20.2 | 10.9 | 11.9 |
| Truncus arteriosus | 3 | 10.3 | 23.3 | 15.0 | 11.3 |
| All | 64 | 0.4 | 23.3 | 11.1 | 12.0 |
| Weight (kg) | | | | | |
| Aortic Arch Anomaly | 2 | 49.0 | 62.6 | 55.8 | 55.8 |
| Cardiomyopathy | 8 | 43.8 | 114.5 | 71.3 | 62.6 |
| Coronary Artery Disease | 9 | 12.0 | 79.3 | 36.9 | 43.3 |
| DORV | 9 | 7.1 | 63.0 | 23.3 | 23.0 |
| Pulmonary Stenosis/Atresia | 4 | 35.5 | 54.5 | 47.1 | 49.1 |
| TGA | 9 | 13.0 | 63.0 | 41.3 | 49.1 |
| TOF | 20 | 3.5 | 124.3 | 42.8 | 38.4 |
| Truncus arteriosus | 3 | 25.0 | 70.5 | 41.5 | 29.0 |
| All | 64 | 3.5 | 124.3 | 43.2 | 43.6 |
| Height (cm) | | | | | |
| Aortic Arch Anomaly | 2 | 142.0 | 179.0 | 160.5 | 160.5 |
| Cardiomyopathy | 8 | 137.0 | 181.0 | 160.0 | 160.0 |
| Coronary Artery Disease | 9 | 97.0 | 169.4 | 144.5 | 155.0 |
| DORV | 9 | 64.5 | 153.0 | 109.4 | 121.0 |
| Pulmonary Stenosis/Atresia | 4 | 136.0 | 162.0 | 152.3 | 155.5 |
| TGA | 9 | 88.0 | 172.0 | 138.1 | 148.0 |
| TOF | 20 | 57.5 | 174.0 | 133.8 | 142.0 |
| Truncus arteriosus | 3 | 133.0 | 173.0 | 153.0 | 153.0 |
| All | 64 | 57.5 | 181.0 | 138.4 | 145.0 |

Example CMR Studies

Imaging studies were performed on either a 1:5 Tesla Philips Achieva or a 3:0 Tesla Philips Ingenia scanner (Philips Healthcare, Best, Netherlands). CMR images for ventricular volume and function analysis were obtained using a standard balanced steady state free precession (SSFP) sequence without the use of a contrast agent. Each dataset includes 12-15 short-axis slices encompassing both right and left ventricles from base to apex with 20-30 frames per cardiac cycle. Typical scan parameters were: slice thickness of 6-10 mm, in-plane spatial resolution of 1:5-2 mm$^2$, repetition time of 3-4 ms, echo time of 1:5-2 ms, and flip angle of 60 degrees. Images were obtained with the patients free breathing; 3 signal averages were obtained to compensate for respiratory motion. Manual image segmentation was performed by a pediatric cardiologist with expertise in cardiac MRI. Endocardial contours were drawn on end-diastolic and endsystolic images. Ventricular volumes and ejection fraction were then computed from these contours. Manual annotations were performed according to SCMR guidelines with Circle cvi42 software (without the use of automated segmentation tools). The ventricular cavity in the basal slice was identified by evaluating wall thickening and cavity shrinking in systole.

Example Post-Processing of CMR Data

Each image's original size and its corresponding segmentation was 512×512 pixels. The original dataset was first preprocessed by center cropping each image to the size 445×445, after removing patients' information and anonymizing the data. To reduce the dimensionality, each cropped image was subsequently resized to 128×128. The entire process was performed using at least one of the two different down-sampling methods: (1) nearest-neighbor down-sampling and/or (2) bi-cubical down-sampling. For training data, twenty-six patients (10 TOFs, 4 DORVs, 4 TGAs, 4 CAAs and 4 patients with cardiomyopathy) were selected whereas the remaining 38 patients were used as test data.

Example Two-Dimensional (2D) Segmentation Using Fully Convolutional Networks

In some embodiments, a fully convolutional network (FCN) is used for an automated pixelwise image segmentation. Convolutional networks are a family of artificial neural networks that are comprised of a series of convolutional and pooling layers in which the data features are learned in various levels of abstraction. These networks are mostly useful when data is either an image or a map such that the proximity among pixels represents how associated they are. While the FCNs can yield high segmentation accuracy for healthy adult CMR images, they performed poorly on Congenital heart disease (CHD) subjects.

FCN Architecture Example

To address such performance issue, a 19-layer FCN for an automated pixelwise image segmentation in CHD subjects is designed. Fine and elementary visual features of an image, e.g., the edges and corners, are learned in the network's shallow layers whereas the coarse semantic information is generated over the deeper layers. These coarse and fine features are combined to learn the filters of the up-sampling layers, which are transposed convolution layers with the kernel size of N (e.g., N=4). The FCN's input can be a 128×128 image and the network's output can be a 128×128 dense heatmap, predicting class membership for each pixel of the input image.

FIG. 1A illustrates an example design architecture of a 19-layer FCN model in accordance with one or more embodiments of the present technology. As shown in FIG. 1, all convolution layers 101 shared the kernel size of 3, stride of 1 pixel with hyperbolic tangent function (Tanh) as their activation function. The input for each convolution layer was padded such that the output has the same length as the original input. To avoid overfitting, l2 regularization was applied to control layer parameters during optimization. To circumvent underfitting, a small regularization coefficient of 0.0005 was selected. These penalties were applied on a per-layer basis and incorporated in the loss function so that the network optimizes during training. Each convolution layer's output was normalized to zero-mean and unit-variance that allows the model to focus on the structural similarities/dissimilarities rather than on the amplitude-driven ones. As shown in FIG. 1, four max-pooling layers P1-P4 with pooling size of 3 were employed to reduce the dimension of the previous layer's output. These coarse and fine features were combined to learn the filters of the up-sampling layers U1-U4 that are transposed convolution layers with the kernel size of 4. The FCN's input is a 128×128 image and the network's output is a 128×128 dense heatmap, predicting class membership for each pixel of the input image.

The FCN model in FIG. 1 includes approximately 11 million parameters. Considering the relatively small CMR image dataset of 527 (570) left (right) ventricle images, the network is prone to overfitting. Therefore, in addition to l2 regularization, three dropout layers that randomly set 50% of the input units to 0 at each update during training were applied after the last convolution layers including 128, 256 and 512 filters.

Despite incorporating l2 regularization and dropout in the FCN architecture, overfitting can still be an issue due to lack of a large set of annotated training data. In some embodiments, the training dataset can be artificially augmented using various image transformations, e.g., affine transformations such as rotation, flipping, and shearing. To conserve the characteristics of the heart chambers, rotation and flipping are used. Transformations such as shearing that instigate shape deformation can be avoided. Each image was first rotated 10 times at angles θ=[0°, 20°, 40°, . . . , 180° ]. Subsequently, each rotated image either remained the same or flipped horizontally, vertically or both. As a result of this augmentation method, the number of training data was multiplied by a factor of 10×4=40.

Example FCN Training Procedure

For the training procedure, the dataset was randomly split into training/validation with the ratio of 0.8/0.2. The validation set was used to provide an unbiased performance estimate of the final tuned model when evaluated over unseen data. Each image was then normalized to zero-mean and unit-variance. In some embodiments, network parameters were initialized according to the Glorot-uniform scheme.

To learn the model parameters, stochastic gradient descent (SGD) can be used with learning rate of 0.002 and moment of 0.9 to accelerate SGD in the relevant direction and dampens oscillations. To improve the optimization process, Nesterov moment updates can be used to evaluate the gradient at the "look-ahead" position instead of the current position. The network was trained using a batch size of 5 for 450 epochs, e.g., passes over the training dataset, to minimize the negative dice coefficient between the predicted and manual ground-truth segmentation.

Example Deep Convolutional Generative Adversarial Networks to Synthesize 2D CMR Images While classic data augmentation techniques increased the number of training data by a factor of 40, it did not solve the overfitting issue. To mitigate that, generative adversarial networks (GANs) can be used to artificially synthesize CMR images and their corresponding segmentation. GANs are a specific family of generative models used to learn a mapping from a known distribution, e.g., random noise, to the data distribution.

Figure 1B:
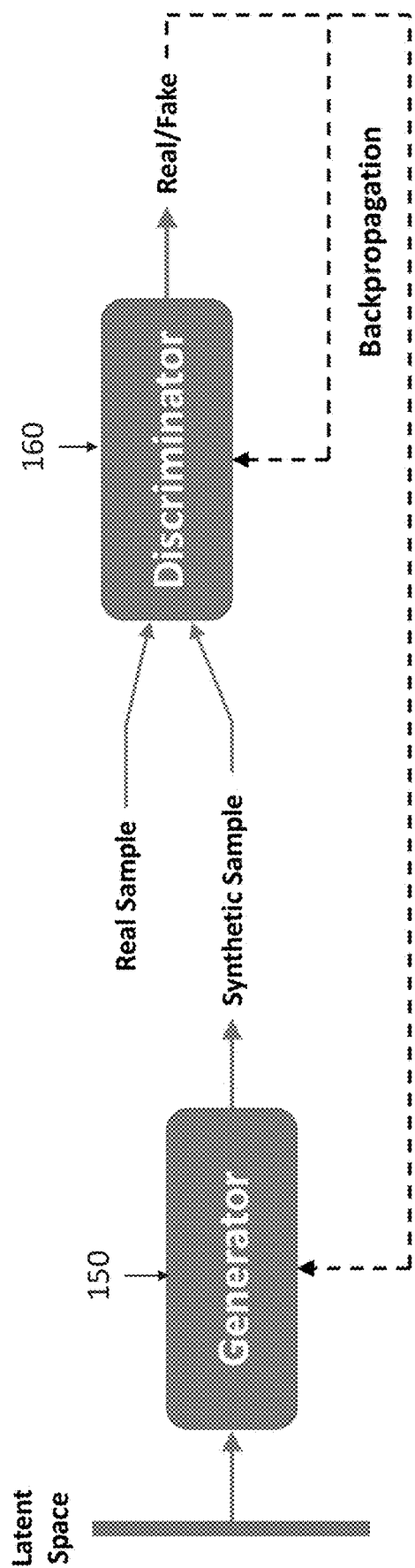
FIG. 1B illustrates an example generative adversarial network (GAN) framework in accordance with one or more embodiments of the present technology.

FIG. 1B illustrates an example generative adversarial network (GAN) framework in accordance with one or more embodiments of the present technology. The adversarial modeling framework is comprised of two components, commonly referred to as the generator 150 and discriminator 160. The functionality of the generator 150 is denoted by a differentiable function, G, which maps the input noise variable z~Pz(z) to a point x=G(z) in the data space. The generator 150 can compete against an adversary, e.g., the discriminator 160, that strives to distinguish between real samples drawn from the genuine CMR data and synthetic samples created by the generator. More precisely, if the functionality of the discriminator is denoted by a differentiable mapping D, then D(x) is a single scalar representing the probability that x comes from the data rather than the generator output. The discriminator 160 is trained to maximize the probability of assigning the correct label to both real and synthetic samples while the generator 150 is simultaneously trained to synthesize samples that the discriminator interprets with high probability as real. More precisely, the discriminator 160 is trained to maximize D(x) when x is drawn from the data distribution $P_{data}$ while the generator 150 is trained to maximize D(G(z)), or equivalently minimize 1−D(G(z)). Hence, adversarial networks are based on a zero-sum non-cooperative game, e.g., a two-player minimax game in which the generator and discriminator are trained by optimizing the following objective function:

$$\min_G \max_D \mathbb{E}_{x \sim P_{data}}[\log D(x)] + \mathbb{E}_{z \sim p_Z}[\log(1 - D(G(z)))] \quad \text{Eq. (1)}$$

Where E represents expectation. The adversarial model converges when the generator and discriminator reach a Nash equilibrium, which is the optimal point for the objective function in Eq. (1). Since both G and D strive to undermine each other, a Nash equilibrium is achieved when the generator recovers the underlying data distribution and the output of D is ubiquitously ½. That is, the discriminator cannot distinguish between real and synthetic data anymore. The optimal generator and discriminator at Nash equilibrium are denoted by G* and D*, respectively. New data samples are generated by feeding random noise samples to the optimal generator G*.

A DCGAN can be designed to synthesize CMR images to augment the training data. The architecture of both generator and discriminator networks along with their training procedures are described next.

DCGAN Architecture Example

Figure 2A:
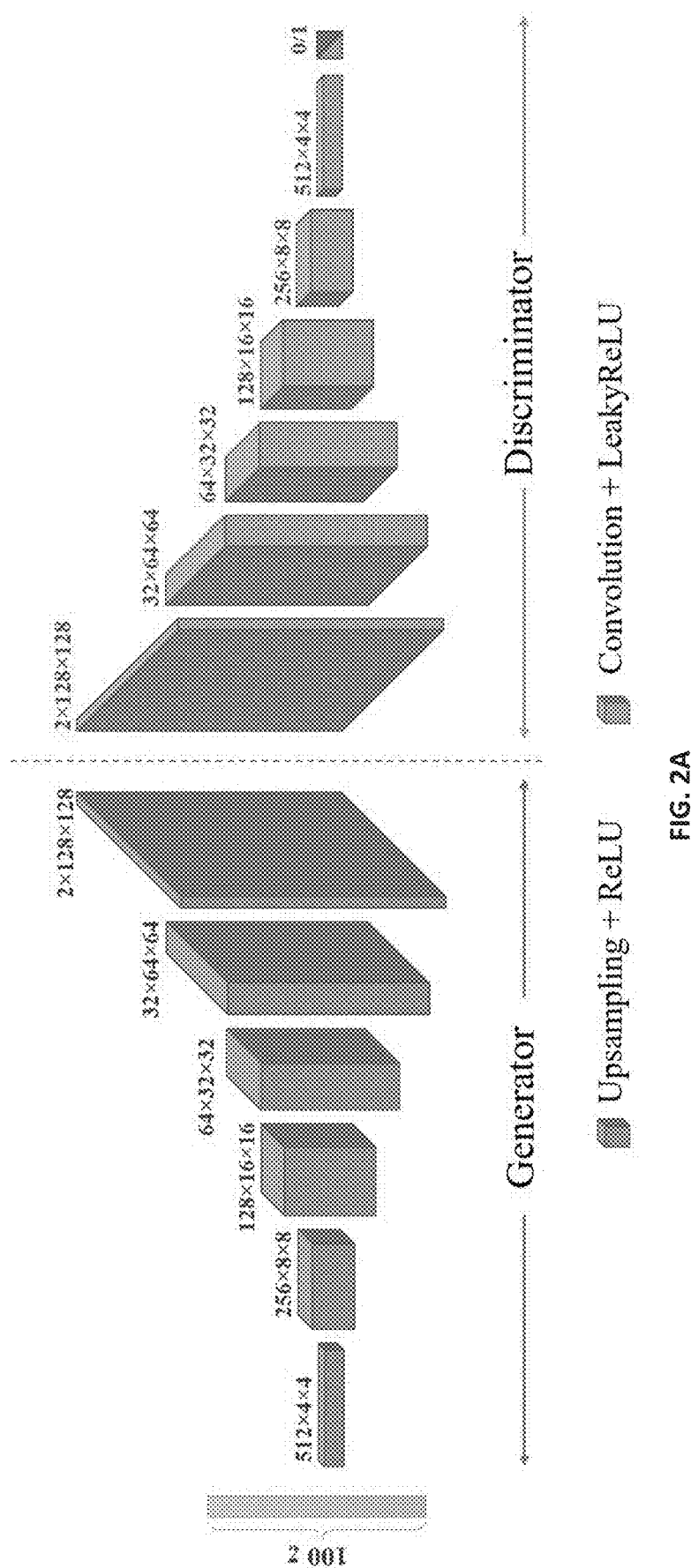
FIG. 2A illustrates an example deep convolutional generative adversarial network (DCGAN) architecture in accordance with one or more embodiments of the present technology.
Figure 2B:
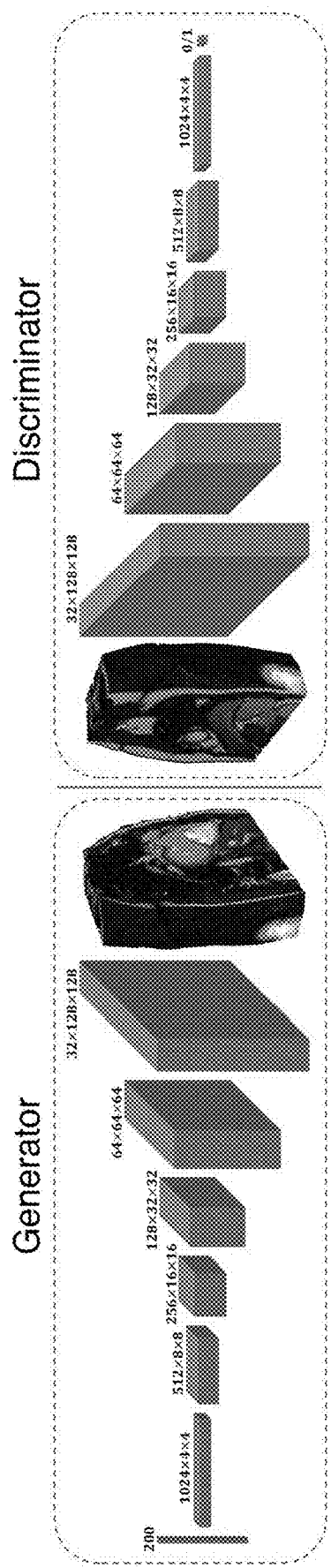
FIG. 2B illustrates an example of three-dimensional (3D) DCGAN architecture in accordance with one or more embodiments of the present technology.

The generator's architecture is shown in FIG. 2A. The input to the generator network was a random noise $z \in R^{100}$ drawn from a standard normal distribution $N(0, I)$. The input was passed through six 2D transposed convolution, also known as fractionally-strided convolution, layers with kernel size of 4×4 to up-sample the input into a 128×128 image. In the first transposed convolution layer, a stride of 1 pixel was used while a stride of 2 pixels was incorporated for the cross-correlation in the remaining layers. The number of channels for each layer is shown in FIG. 2A. All 2D transposed convolution layers except the last one were followed by a Rectified linear unit (ReLU) activation layer. The last layer was accompanied by a Tanh activation function. The generator network's output included two channels where the first channel is for the synthetic CMR image and the second channel contains the corresponding segmentation mask.

The discriminator network's architecture is a deep convolutional neural network shown in FIG. 2A. The discriminator network's input was a 2×128×128 image while its output was a scalar representing the probability that its input is a real pair of images and the corresponding segmentation mask. The model was composed of six 2D convolution layers with kernel size of 4×4 and stride of 2 pixels except for the last layer for which a 1-pixel stride value was used. The number of channels for each convolution layer is shown in FIG. 2A. All layers except the last one were followed by a Leaky ReLU activation layer with negative slope value of 0.2. The last layer was accompanied by a sigmoid function.

Example DCGAN Training Procedure

The training data was normalized to zero-mean and unit-variance to stabilize the DCGAN learning process. Each training sample was then rotated 19 times at angles $\theta = [0°, 10°, 20°, \ldots, 180°]$. Each rotated image either remained the same or flipped horizontally, vertically or both. As a result of this augmentation process, the number of training data was multiplied by a factor of 19×4=76.

The DCGAN's two known issues are mode collapse and gradient vanishing. Mode collapse is the case that too many values of the input noise, z, are mapped to the same value of x in the data space. This happens when the generator is over-trained with respect to the discriminator. Gradient vanishing refers to the case that the discriminator becomes too successful in distinguishing the real from synthetic images with no gradient is back-propagated to the generator. In this case, the generator network cannot learn to generate synthetic images that are similar to the real images. To address these concerns, first, the network parameters were initialized according to a Gaussian distribution with zero-mean and variance of 0.02. To learn the network parameters, Adam optimizer can be used for both generator and discriminator networks. The learning rate, parameter $\beta_1$, and parameter $\beta_2$ in Adam optimizer were set to 0.0002, 0.5, and 0.999, respectively. The binary cross entropy between the target and the output was minimized.

Because Adam, like any other gradient-based optimizer, is a local optimization method, only a local Nash equilibrium can be established between the generator and discriminator. A common method to quantify the quality of the generated synthetic samples is the Frechet Inception Distance (FID). In FID, features of both real and synthetic data are extracted via a specific layer of Inception v3 model. These features are then modeled as multivariate Gaussian, and the estimated mean and covariance parameters are used to calculate the distance as:

$$FID(s, r) = \|\mu_s - \mu_r\|_2^2 + Tr\left(\sum_s + \sum_r - 2\left(\sum_s \sum_r\right)^{\frac{1}{2}}\right) \quad \text{Eq. (2)}$$

where $(\mu_s, \Sigma_s)$ and $(\mu_r, \Sigma_r)$ are the mean and covariance of the extracted feature from the synthetic and real data, respectively. Lower FID values indicate better image quality and diversity among the set of synthetic samples. Once the locally optimal generator was obtained, various randomly-selected subsets of the generated synthetic images were considered and the one with the lowest FID distance to the set of real samples was chosen.

In some embodiments, each iteration of the learning procedure included the following two steps:

First, a single optimization step was performed to update the discriminator. A batch of 5 real image samples and their corresponding segmentation masks from the training data was randomly selected. Label 1 was assigned to them since they are real samples. These pairs of real images and their masks were then passed through the discriminator network and the gradient of the loss, e.g., the binary cross entropy between predicted and true labels, was back-propagated to accordingly adjust the discriminator weights. Then, a batch of 5 noise samples was drawn from the standard normal distribution and passed through the generator network to create 5 pairs of images and their corresponding masks. These pairs were then labeled with 0 since they were synthetic samples. This batch of synthetic data was then passed through the discriminator and the gradient of the loss was back-propagated to fine-tune the discriminator weights.

Second, an additional optimization step was performed to update the generator. Each pair of synthetic image and its corresponding segmentation mask from the previous step was labeled 1 to mislead the discriminator and create the perception that the pair is real. These samples were then passed through the discriminator and the gradient of the loss was back-propagated to adjust the generator weights.

In summary, in the first step, the discriminator was fine-tuned while the generator was unchanged, and in the second step, the generator was trained while the discriminator remained unchanged. The training process continued for 40,000 iterations, or until the model converged and an equilibrium between the generator and discriminator networks was established.

DCGAN Post-Processing Example

The pixel value in each real mask is either 1 or 0 implying whether each pixel belongs to one of the ventricles or not. Therefore, the value of each pixel in a synthesized mask was quantized to 0 when it was less than 0.5 and rounded up to 1 otherwise.

To avoid very small or large mask areas, only the synthetic samples for which the ratio of the mask area to the total area was within a certain range were retained. For nearest-neighbor down-sampling, the range was between 0.005 and 0.025 while for the bi-cubical down-sampling, the range was between 0.02 and 0.05. Finally, the connected components in each binary mask were located. If there were more than one connected component and the ratio of the area of the largest component to the second largest component was less than 20, that pair of image and mask would be removed from the set of synthetically-generated data.

Example 3D Image Segmentation Using Fully Convolutional Networks

As a further extension of the 2D architecture presented above, a deep fully convolutional network for an automated 3D segmentation of left and right ventricles was also developed. Affine transformations that do not cause shape deformation, e.g. rotation and flipping, can be used for data augmentation. While geometric data augmentation improves the segmentation accuracy, the performance of the network is still limited due to the limited set of features that geometric transformations can introduce. To mitigate that, generative adversarial networks (GANs) can be used to artificially synthesize 3D CMR images and their corresponding segmentation.

Example Deep Convolutional Generative Adversarial Networks to Synthesize 3D CMR Images A data generating process can be implemented to create synthetic segmented images from the data distribution. In some embodiments, a 3D deep convolutional generative adversarial network can be used to learn a mapping from a standard normal distribution to the joint distribution of 3D images and their corresponding masks. One example of such a network is shown in FIG. 3B. The network includes two blocks that are trained in an adversarial manner: (a) the Generator, which creates synthetically segmented hearts from noise samples; and (b) the Discriminator, which distinguishes between real segmented data and those that are created artificially by the generator. The training is continued until an equilibrium is established between the two networks. The optimal generator can then be used for synthetic data augmentation by creating real-looking segmented data from noise samples.

Different performance metrics and clinical indices for the fully-automatic method where compared to those of manual segmentation by expert physician as the ground-truth. Furthermore, the same indices calculated by the commercially available cvi42 software were used for head-to-head performance comparison. The synthetically generated CMR images and the corresponding automatically-generated segmentation masks are also presented herein.

In one example aspect, a generative adversarial network includes a generator configured to generate synthetic medical images attributed to a cardiovascular system. The generator has parameters that have been initialized according to a predetermined probability distribution. The generative adversarial network also includes a discriminator configured to receive the synthetic medical images from the generator and determine probabilities indicating likelihood of the synthetic imaging samples corresponding to real cardiovascular images acquired from an individual (e.g., a patient or a test subject). The discriminator has parameters that have been initialized according to the predetermined probability distribution. As shown in FIG. 1B, the discriminator is further configured to provide the probabilities determined by the discriminator to the generator and the discriminator (e.g., backpropagation) to allow the parameters of the generator and the parameters of the discriminator to be adjusted iteratively until an equilibrium between the generator and the discriminator is established.

In some embodiments, the predetermined probability distribution consists of a Gaussian distribution. In some embodiments, the parameters of the generator and the parameters of the discriminator are initialized with a mean value of 0 and a variance of 0.02.

In some embodiments, the generative adversarial network is configured to adjust the parameters of the generator and the parameters of the discriminator based on adjusting the parameters of the discriminator based on a first set of probabilities generated by the discriminator. The first set of probabilities are generated using a first set of imaging samples designated as real cardiovascular samples of a person and a second set of imaging samples designated as synthetic samples generated by a computer system. The generative adversarial network is further configured to adjust the parameters of the generator and the parameters of the discriminator based on adjusting the parameters of the generator based on a second set of probabilities generated by the discriminator. The second set of probabilities are generated using a third set of synthetic imaging samples designated as real cardiovascular samples. In some embodiments, the parameters of the generator remain unchanged when the parameters of the discriminator are adjusted, and the parameters of the discriminator remain unchanged when the parameters of the generator are adjusted.

In some embodiments, the generator is configured to output two channels comprising a first channel that outputs information representing the synthetic medical images and a second channel that outputs information representing segmentation masks corresponding to the synthetic medical images.

In some embodiments, the generative adversarial network is part of a neural network system. The neural network system is configured to receive an initial set of image data and provide an augmented set of image data using the synthetic imaging samples generated by the generative adversarial network. The neural network system further includes an additional neural network configured to perform segmentation on the augmented set of image data. In some embodiments, the additional neural network comprises a fully convolutional neural network. In some embodiments, the initial set of image data is associated with a congenital heart disease, the initial set of image data including one or more of: magnetic resonance image data, echocardiography data, or computed tomography (CT) image data. In some embodiments, the initial set of image data includes two-dimensional image data, and the augmented set of image data includes three-dimensional image data generated based on the two-dimensional image data.

In some embodiments, the generative adversarial network is configured to synthesize data associated with a heart's left ventricle. The neural network system further comprises another generative adversarial network configured to synthesize image data associated with at least one or more of: heart's right ventricle, right atrium or left atrium.

Example Network Training and Testing

Fully Convolutional Networks Using Traditional Dataset

For each chamber, one FCN was trained on the CMR images of 26 patients and their augmentation via geometric transformations. Each model was jointly trained on both end-diastolic (ED) and end-systolic (ES) images for each chamber. These networks are called LV-FCN and RV-FCN in the results section.

Fully Convolutional Networks Using Synthetically Augmented Dataset

Two separate DCGAN models were designed for Left Ventricle (LV) and Right Ventricle (RV) to further augment the training data. Additional models can be trained for Right Atrium (RA) or Left Atrium (LA). The designed DCGAN was used to generate 6,000 pairs of synthetic images and segmentation masks. Applying the DCGAN post-processing step, a set of 2,500 synthetic sample images, out of the 6,000 generated pairs, was used for each chamber. Each of the 2,500 selected images was then either remained the same, or flipped horizontally, vertically, or rotated 4 times at angles θ=[45°, 90°, 135°, 180° ]. Thus, 2,500×7=17,500 synthetic CMR images and their corresponding segmentation masks were obtained for each ventricle. Finally, our synthetically augmented repertoire included the CMR images of 26 patients and their augmentation via geometric transformations plus the generated 17,500 synthetic CMR images. Using this synthetically augmented dataset, another FCN was trained for each chamber. Each model was jointly trained on both ED and ES images. The networks designed using the synthetically augmented dataset (SAD) are called LV-FCN-SAD and RV-FCN-SAD in the results section.

U-Net Architecture

Figure 3:
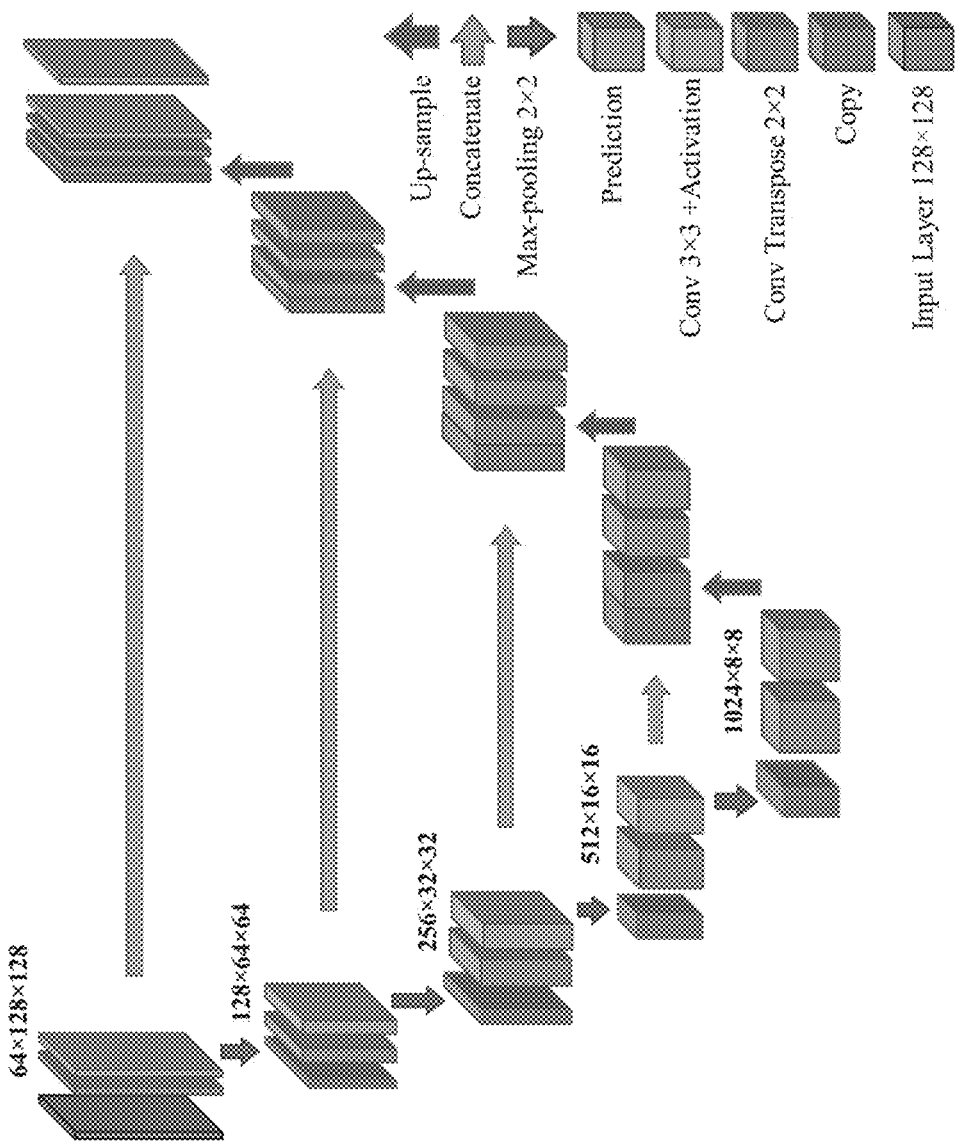
FIG. 3 illustrates an example architecture of the U-Net model.
Figure 6D:
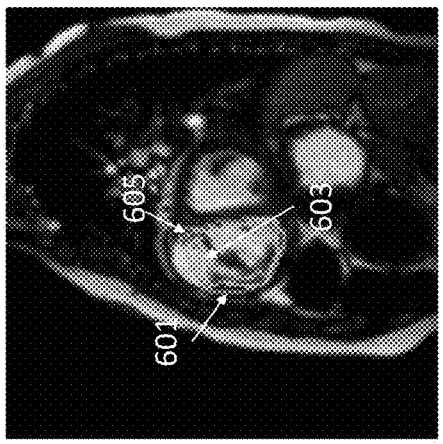
FIG. 6D illustrates yet another sample segmentation result.
Figure 6C:
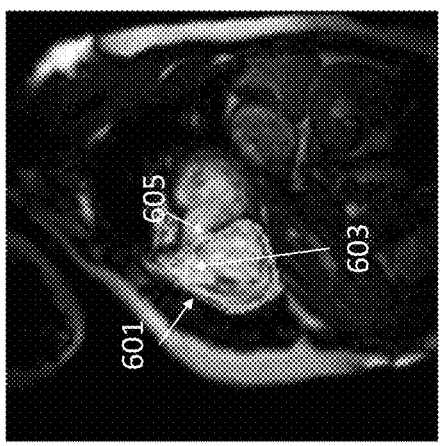
FIG. 6C illustrates another sample segmentation result.
Figure 6B:
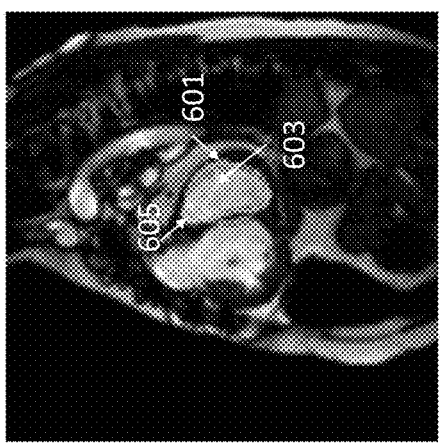
FIG. 6B illustrates another sample segmentation result.
Figure 6A:
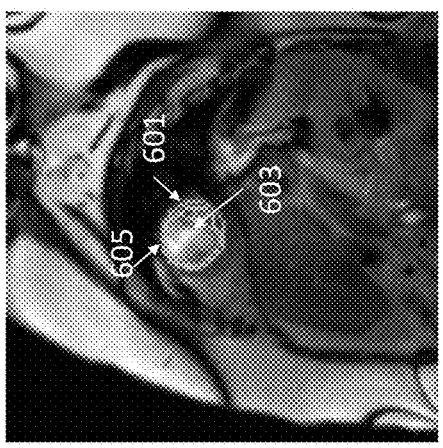
FIG. 6A illustrates a sample segmentation result.

In addition to the network architecture described above, a traditional U-Net model can be designed to compare its results with the designed FCNs. In some implementations, a customized U-Net architecture with the input size of 128× 128 was used. FIG. 3 illustrates an example architecture of the U-Net model. Similar to the case of our FCN, for each chamber, a network was trained on the training set of 26 patients and its augmentation via geometric transformations. In the results section, these networks are referred to as LV-UNet and RV-UNet. For each chamber, another network was trained on the synthetically segmented CMR images, as was used for designing FCN-SAD. These networks are referred to as LV-UNet-SAD and RV-UNet-SAD. Each network was jointly trained on both ED and ES images for each chamber.

Commercially Available Segmentation Software

The results generated by these models were compared with results from cvi42 by Circle Cardiovascular Imaging Inc. (Calgary, Canada) on the test set that included CMR images from 38 patients. All volumetric measures were calculated using OsiriX Lite software (Bernex, Switzerland). The segmented CMR images were converted into OsiriX's .roi files using the modified plugin. The resulted .ori files were imported to the OsiriX Lite software for volume calculation through its build-in 3D construction algorithm.

Metrics for Performance Verification

There are two different classes of metrics to compare the performance of cardiac chamber segmentation methods. One class uses the important clinical indices, such as volumetric data that are important for clinical decision making. These indices may not identify the geometric point-by-point differences between automated and manually delineated segmentation.

Another class of indices uses geometric metrics that are indications of how mathematically close the automatic segmentation is to that of the ground-truth. These include the average Dice metric, Jaccard indices, Hausdorff distance (HD) and mean contour distance (MCD). The Dice and Jaccard are two measures of contour overlap with a range from zero to one where a higher index value indicates a better match between the predicted and true contours:

$$\text{Dice} = \frac{2|A \cap B|}{|A|+|B|}, \quad \text{Jaccard} = \frac{|A \cap B|}{|A \cup B|} \quad \text{Eq. (3)}$$

where A and B are true and predicted segmentation, respectively. Hausdorff and mean contour distances are two other standard measures that show how far away the predicted and ground-truth contours are from each other. These metrics are defined as:

$$HD = \max\left(\max_{a \in \partial A} d(a, \partial B), \max_{b \in \partial B} d(b, \partial A)\right), \quad \text{Eq. (4)}$$

$$MCD = \frac{1}{2|\partial A|}\sum_{a \in \partial A} d(a, \partial B) + \frac{1}{2|\partial B|}\sum_{b \in \partial B} d(b, \partial A),$$

where ∂A and ∂B denote the contours of the segmentation A and B, respectively, and d(a, ∂B) is the minimum Euclidean distance from point a to contour ∂B. The lower values for these metrics indicate better agreement between automated and manual segmentation.

The ICC for paired data values $(x_i, x'_i)$, for i=1, ..., N, a descriptive statistic that quantifies the similarity of the samples in the same group, is defined as:

$$r = \frac{1}{Ns^2}\sum_{i=1}^{N}(x_i - \bar{x})(x'_i - \bar{x}), \quad \text{Eq. (5)}$$

Where $$\bar{x} = \frac{1}{2N}\sum_{i=1}^{N}(x_i + x'_i), \quad \text{Eq. (6)}$$

$$s^2 = \frac{1}{2N}\left(\sum_{i=1}^{N}(x_i - \bar{x})^2 + \sum_{i=1}^{N}(x'_i - \bar{x})^2\right). \quad \text{Eq. (7)}$$

Performance Verification and Comparison to the Clinically Used Software

The results were compared head-to-head with U-Net and commercially-available cvi42, which is trained on the UK Biobank data and is clinically being used. Two different classes of metrics are used to compare the performance of cardiac chamber segmentation methods. One class uses the clinical indices, such as volumetric data that are crucial for clinical decision making. These indices may not identify the geometric point-by-point differences between automated and manually delineated segmentations. Another class of indices uses geometric metrics that indicate how mathematically close the automatic segmentation is to that of the ground-truth. These include the average Dice metric, Jaccard index, Hausdorff distance (HD) and mean contour distance (MCD).

Generalizability to Additional Training and Test Subjects

To evaluate the generalizability of the framework on subjects not included in the dataset, the disclosed methods have been tested on the 2017 MICCAI's Automated Cardiac Diagnosis Challenge (ACDC). The ACDC dataset includes 100 subjects: (i) healthy (n=20); (ii) previous myocardial infarction (n=20); (iii) dilated cardiomyopathy (n=20); (iv) hypertrophic cardiomyopathy (n=20); and (v) abnormal right ventricle (n=20). For a consistent image size, five subjects were removed and the remaining 95 subjects were zero-padded to 256×256, and then down-sampled to 128× 128 using nearest-neighbor down-sampling method. Three subjects from each group were randomly selected as training data and the remaining 80 subjects were left as the test data.

For each chamber, one FCN was trained on the combined CMR images of both training sets, e.g., 26 patients from our dataset and 15 from the ACDC dataset, and their augmentation via geometric transformations. For each heart chamber, another FCN is trained on the dataset that is further augmented via previously generated set of synthetically segmented CMR images. Each model was jointly trained on both ED and ES images for each heart chamber. The first and second segmentation networks are referred to as FCN-2.0 and FCN-SAD-2.0, respectively. FCN-2.0 and FCN-SAD-2.0 were evaluated on the combined set of test subjects, e.g., 38 patients from our dataset and 80 patients from the ACDC dataset.

Statistical Methods

Paired student t-test and intraclass correlation coefficient (ICC) were used for statistical analysis of predicted volumes. The p-value for the paired student t-test can be interpreted as the evidence against the null hypothesis that predicted and ground-truth volumes have the same mean values. A p-value greater than 0.05 is considered as passing the statistical hypothesis testing. The intraclass correlation coefficient describes how strongly the measurements within the same group are similar to each other. The intraclass correlation f was used, which focuses on the paired predicted and ground-truth measurements. The following guidelines were used to interpret the ICC values: (a) less than 0.5: poor; (b) between 0.50 and 0.75: moderate; (c) between 0.75 and 0.90: good; and (d) more than 0.90: excellent.

Example Real and Synthetically-Generated 2D CMR Images

A sample batch of real CMR images, including their manually segmented LV masks 401, as shown in FIG. 4A is compared with a sample batch of synthetically-generated CMR images with their corresponding automatically-generated LV masks as shown in FIG. 4B. Similar comparison has been made for RV with manually segmented RV masks 501 as shown in FIG. 5A and FIG. 5B.

Example Segmentation Performance

As mentioned above, two separate down-sampling methods—nearest-neighbor and bi-cubical—were practiced and training/testing was independently performed on the results of each.

Example Segmentation Performance for Nearest-Neighbor Down-Sampling

The average Dice metric, Jaccard indices, Hausdorff distance (HD), mean contour distance (MCD) and correlation $R_{vol}^2$ for FCN and FCN-SAD computed based on the ground-truth are reported in Table 3 below.

TABLE 3

Mean (SD) of different quantitative metrics for nearest-neighbor down-sampling

|  | Dice (%) | Jaccard | HD (mm) | MCD (mm) | R2vol (%) |
|---|---|---|---|---|---|
| | | | LVED | | |
| FCN | 86.47 (22.20) | 80.68 (23.50) | 6.92 (12.08) | 2.31 (6.43) | 98.47 |
| FCN-SAD | 90.63 (13.75) | 84.89 (16.49) | 5.04 (7.42) | 1.68 (3.81) | 99.26 |
| cvi42 | 73.17 (34.25) | 66.52 (32.97) | 7.52 (13.56) | 3.43 (10.79) | 78.59 |
| U-Net | 84.50 (24.37) | 78.44 (25.39) | 7.22 (10.24) | 3.32 (8.47) | 93.40 |
| U-Net-SAD | 87.08 (21.89) | 81.44 (22.62) | 6.66 (10.80) | 2.33 (7.14) | 97.89 |
| | | | LVES | | |
| FCN | 83.15 (20.93) | 75.09 (22.46) | 6.89 (12.03) | 2.71 (7.41) | 92.96 |
| FCN-SAD | 84.96 (18.83) | 77.26 (21.18) | 6.33 (9.43) | 2.52 (5.63) | 96.59 |
| cvi42 | 70.98 (32.24) | 62.57 (30.53) | 7.93 (15.25) | 3.96 (13.34) | 76.59 |
| U-Net | 79.42 (25.23) | 71.22 (26.06) | 7.14 (10.06) | 2.74 (6.77) | 82.17 |
| U-Net-SAD | 82.27 (20.87) | 73.79 (22.46) | 7.58 (11.88) | 2.53 (6.70) | 92.29 |
| | | | RVED | | |
| FCN | 80.25 (23.95) | 71.92 (24.91) | 14.20 (15.71) | 6.64 (13.63) | 86.96 |
| FCN-SAD | 84.44 (20.16) | 76.74 (21.47) | 10.67 (11.52) | 3.76 (6.46) | 95.91 |
| cvi42 | 54.29 (40.88) | 47.80 (37.82) | 15.76 (17.78) | 5.60 (9.04) | 31.87 |
| U-Net | 77.68 (27.05) | 69.58 (27.89) | 15.09 (19.32) | 5.72 (14.24) | 84.15 |
| U-Net-SAD | 81.83 (22.53) | 73.68 (23.71) | 12.29 (14.10) | 4.10 (7.11) | 93.36 |
| | | | RVES | | |
| FCN | 74.66 (24.53) | 64.37 (24.94) | 13.63 (19.85) | 6.06 (16.32) | 87.55 |
| FCN-SAD | 79.22 (20.09) | 69.12 (21.61) | 11.19 (12.48) | 4.09 (7.64) | 93.34 |
| cvi42 | 53.70 (38.00) | 45.46 (33.98) | 12.88 (12.47) | 4.66 (5.79) | 64.30 |
| U-Net | 71.33 (28.09) | 61.40 (27.70) | 14.64 (18.98) | 6.09 (15.97) | 88.37 |
| U-Net-SAD | 74.79 (24.77) | 64.56 (24.85) | 12.13 (12.97) | 4.16 (6.63) | 88.72 |

The Dice metrics for FCN method were 86.47%, 83.15%, 80.25% and 74.66% for LVED, LVES, RVED and RVES, respectively. The corresponding Dice metrics for FCN-SAD method were 90.63%, 84.96%, 84.44% and 79.22%, respectively.

Sensitivity, specificity, positive predictive value (PPV) and negative predictive value (NPV) are summarized in Table 4.

TABLE 4

Mean (SD) of different statistical metrics for nearest-neighbor down-sampling

|  | Sensitivity (%) | Specificity (%) | PPV (%) | NPV (%) |
|---|---|---|---|---|
| LVED | | | | |
| FCN | 85.70 (22.73) | 99.85 (0.37) | 89.54 (21.91) | 99.78 (0.32) |
| FCN-SAD | 91.73 (13.37) | 99.87 (0.18) | 90.93 (15.54) | 99.85 (0.17) |
| cvi42 | 79.47 (35.68) | 99.58 (0.66) | 69.77 (34.18) | 99.69 (0.59) |
| U-Net | 83.04 (25.88) | 99.91 (0.12) | 89.71 (21.94) | 99.76 (0.29) |
| U-Net-SAD | 86.84 (22.17) | 99.89 (0.15) | 89.22 (21.99) | 99.82 (0.20) |
| LVES | | | | |
| FCN | 82.91 (22.65) | 99.89 (0.22) | 86.44 (22.42) | 99.83 (0.24) |
| FCN-SAD | 88.49 (18.96) | 99.85 (0.26) | 84.70 (20.80) | 99.90 (0.12) |
| cvi42 | 79.57 (33.80) | 99.67 (0.57) | 66.97 (32.52) | 99.82 (0.34) |

TABLE 4-continued

Mean (SD) of different statistical metrics for nearest-neighbor down-sampling

|  | Sensitivity (%) | Specificity (%) | PPV (%) | NPV (%) |
|---|---|---|---|---|
| U-Net | 78.95 (27.48) | 99.90 (0.16) | 84.10 (26.03) | 99.83 (0.20) |
| U-Net-SAD | 82.12 (23.39) | 99.89 (0.15) | 87.05 (20.64) | 99.84 (0.19) |
| RVED | | | | |
| FCN | 79.62 (25.37) | 99.73 (0.34) | 84.41 (22.55) | 99.56 (0.55) |
| FCN-SAD | 84.89 (21.45) | 99.72 (0.39) | 86.24 (20.33) | 99.69 (0.38) |
| cvi42 | 53.09 (41.31) | 99.71 (0.51) | 60.15 (42.39) | 98.96 (1.14) |
| U-Net | 77.02 (29.43) | 99.73 (0.36) | 84.14 (23.53) | 99.57 (0.56) |
| U-Net-SAD | 80.95 (24.64) | 99.75 (0.32) | 86.28 (20.64) | 99.60 (0.53) |
| RVES | | | | |
| FCN | 75.01 (26.56) | 99.72 (0.42) | 79.50 (25.05) | 99.69 (0.32) |
| FCN-SAD | 83.47 (19.97) | 99.62 (0.58) | 79.03 (22.97) | 99.78 (0.24) |
| cvi42 | 54.31 (39.54) | 99.67 (0.54) | 57.27 (38.95) | 99.36 (0.74) |
| U-Net | 70.84 (30.32) | 99.76 (0.35) | 77.68 (27.80) | 99.65 (0.35) |
| U-Net-SAD | 74.17 (27.13) | 99.76 (0.32) | 80.34 (24.29) | 99.68 (0.31) |

For both methods, average absolute and average relative deviation of the automatically-segmented volumes from manually-segmented volumes, stroke volumes and ejection fractions are reported in Table 5. A smaller deviation indicates better conformity between automatically- and manually-derived contours.

TABLE 5

Mean (SD) of the volume/SV/EF differences between predicted and manual segmentations for nearest-neighbor down-sampling.

|  | FCN | FCN-SAD | cvi42 | U-Net | U-Net-SAD |
|---|---|---|---|---|---|
| Absolute difference | | | | | |
| LVEDV (mL) | 4.57 (3.95) | 2.88 (3.05) | 12.75 (18.76) | 8.31 (9.30) | 5.29 (4.67) |
| LVESV (mL) | 3.55 (3.92) | 2.68 (2.52) | 6.34 (7.27) | 5.32 (6.45) | 3.85 (3.93) |
| RVEDV (mL) | 12.03 (18.65) | 7.65 (9.77) | 30.31 (40.62) | 12.61 (20.70) | 9.37 (12.58) |
| RVESV (mL) | 6.66 (8.28) | 5.42 (5.56) | 9.81 (15.12) | 6.66 (7.71) | 5.68 (8.28) |
| LVSV (mL) | 3.67 (3.60) | 2.17 (1.83) | 10.47 (17.72) | 4.09 (4.67) | 3.01 (2.84) |
| RVSV (mL) | 9.61 (13.13) | 5.98 (6.77) | 22.41 (28.28) | 10.57 (15.84) | 6.93 (7.56) |
| LVEF (%) | 4.08 (4.86) | 2.84 (1.86) | 107.8 (613.28) | 4.75 (6.45) | 5.36 (14.06) |
| RVEF (%) | 4.06 (2.97) | 3.74 (3.03) | 48.47 (193.00) | 4.50 (4.82) | 3.49 (3.30) |
| Relative difference | | | | | |
| LVEDV (%) | 7.09 (11.36) | 4.00 (5.70) | 21.07 (32.54) | 10.66 (16.42) | 8.09 (15.55) |
| LVESV (%) | 12.84 (14.10) | 9.46 (7.61) | 28.91 (56.94) | 17.06 (19.45) | 13.50 (16.93) |
| RVEDV (%) | 10.43 (14.14) | 7.38 (8.73) | 26.96 (28.49) | 12.13 (18.17) | 8.78 (10.74) |
| RVESV (%) | 13.91 (15.60) | 12.46 (12.41) | 24.89 (28.36) | 14.72 (16.26) | 11.18 (11.58) |
| LVSV (%) | 8.84 (13.41) | 5.05 (6.79) | 26.68 (35.23) | 9.85 (16.55) | 8.34 (16.08) |
| RVSV (%) | 13.46 (14.29) | 9.41 (9.03) | 32.59 (32.52) | 15.84 (20.03) | 11.14 (12.11) |
| LVEF (%) | 6.87 (8.06) | 4.63 (2.88) | 182.23 (1036.04) | 7.84 (10.84) | 9.16 (23.76) |
| RVEF (%) | 7.07 (5.29) | 6.44 (5.22) | 89.26 (366.26) | 7.44 (7.48) | 5.73 (5.03) |

The ranges of left ventricular end-diastolic volume (LVEDV), end-systolic volume (LVESV), stroke volume (LVSV) and ejection fraction (LVEF) were (10 mL to 202 mL), (4 mL to 91 mL), (6 mL to 128 mL) and (30% to 75%), respectively. The ranges of right ventricular end-diastolic volume (RVEDV), end-systolic volume (RVESV), stroke volume (RVSV) and ejection fraction (RVEF) were (20 mL to 265 mL), (6 mL to 130 mL), (12 mL to 138 mL) and (32% to 84%), respectively.

The p-values for the paired sample t-test of LVEDV, LVESV, RVEDV and RVESV, to test the null hypothesis that are predicted and ground-truth volumes have identical expected values are tabulated in Table 6. A p-value greater than 0.05 is considered as passing the t-test and is boldfaced in Table 6.

TABLE 6

ICC and P-values of the paired sample t-test for models trained on nearest-neighbor down-sampled data.

|  | FCN | FCN-SAD | cvi42 | U-Net | U-Net-SAD |
|---|---|---|---|---|---|
|  |  | P-Value |  |  |  |
| LVEDV | 7.428e−6 | 4.438e−3 | 0.2887 | 1.278e−4 | 9.886e−4 |
| LVESV | 1.440e−4 | 0.3967 | 0.0146 | 1.284e−3 | 8.218e−4 |
| RVEDV | 0.0103 | 0.1228 | 5.181e−5 | 3.026e−2 | 4.666e−3 |
| RVESV | 0.0537 | 0.5481 | 3.912e−3 | 5.535e−4 | 4.136e−3 |
|  |  | ICC |  |  |  |
| LVEDV | 0.9922 | 0.9963 | 0.8928 | 0.9637 | 0.9891 |
| LVESV | 0.9623 | 0.9824 | 0.8934 | 0.8964 | 0.9566 |
| RVEDV | 0.9307 | 0.9793 | 0.6430 | 0.9206 | 0.9640 |
| RVESV | 0.9359 | 0.9672 | 0.8190 | 0.9367 | 0.9358 |

Example LV and RV segmentations at end-systole and end-diastole are shown in FIGS. 6A-D. Red contours 601 correspond to the ground-truth (e.g., manual annotation by the expert pediatric cardiologist) whereas green 603 and yellow 605 contours correspond to the predicted delineations by FCN and FCN-SAD methods, respectively.

The correlation and Bland-Altman plots are shown in FIGS. 7A to 10D. The FCN and FCN-SAD results are depicted by red and blue dots, respectively. As shown in FIGS. 7A to 8D, the points deviated from the line y=x are due to the mismatch between prediction and ground-truth. The Bland-Altman figures are commonly used to evaluate the agreement among clinical measures and identification of any systematic difference (e.g., fixed bias, outliers etc.) between them. The bias values of the FCN for LVEDV, LVESV, RVEDV and RVESV were 3.91 mL, 3.00 mL, 8.93 mL and 3.28 mL, respectively, whereas the bias values of the FCN-SAD for LVEDV, LVESV, RVEDV and RVESV were 1.86 mL, 0.51 mL, 3.09 mL and −0.77 mL, respectively. The 95% confidence interval of difference between automatic segmentation and ground-truth is shown via dashed lines representing ±1.96 standard deviation. FIGS. 9A to 10D indicate that applying the FCN-SAD method reduced the mean and standard deviation of error and tightened the confidence interval compared to the FCN method.

Example Segmentation Performance for Bi-Cubical Down-Sampling

The results for the bi-cubical down-sampling method are reported in Table V. FCN-SAD method's Dice metrics for LVED, LVES, RVED and RVES were 91.03%, 86.82%, 84.70% and 80.57%, respectively. The FCN-SAD's t-test p-values for LVED, LVES, RVED and RVES are 0.2739, 0.0945, 0.0858, and 0.6585, respectively. FCN-SAD method unequivocally passes the paired sample t-test for LV and RV at both end-diastolic and end-systolic phases.

TABLE V

|  | Dice (%) | Jaccard (%) | Rel. volume difference (%) | $R_{vol}^2$ (%) | t-test p-value |
|---|---|---|---|---|---|
| (a) FCN |  |  |  |  |  |
| LVED | 88.40 (18.44) | 82.59 (20.27) | 6.03 (10.31) | 98.54 | 0.0147 |
| LVES | 83.10 (22.61) | 75.61 (23.80) | 10.07 (9.31) | 95.70 | 0.0786 |
| RVED | 80.93 (22.90) | 72.57 (24.30) | 9.28 (14.24) | 87.71 | 0.0159 |
| RVES | 77.23 (22.84) | 67.22 (23.63) | 13.55 (15.58) | 90.55 | 0.0226 |
| (b) FCN-SAD |  |  |  |  |  |
| LVED | 91.03 (14.94) | 85.82 (17.04) | 4.58 (0.06) | 99.24 | 0.2739 |
| LVES | 86.82 (16.45) | 79.40 (18.88) | 7.87 (5.08) | 97.84 | 0.0945 |
| RVED | 84.70 (18.79) | 76.78 (20.76) | 6.77 (8.63) | 94.85 | 0.0858 |
| RVES | 80.57 (19.71) | 70.90 (21.20) | 11.02 (13.75) | 92.85 | 0.6585 |

The correlation and Bland-Altman plots for end-systolic and end-diastolic ventricular volumes, ejection fractions and stroke volumes for the bi-cubical down-sampling method are depicted in FIGS. 11A-14D.

Example Segmentation Performance for cvi42

The cvi42 resulted Dice metrics were 73.17%, 70.98%, 54.29% and 53.70% for LVED, LVES, RVED and RVES, respectively. The absolute and relative deviations of automatically—from manually-segmented results for LV and RV volumes at ED and ES as well as SV and EF are summarized in the last column of Table III. The correlation and Bland-Altman plots for cvi42 are shown by green dots in FIGS. 7A to 10D. The bias values of the cvi42%-derived volume deviation from the ground-truth for LVEDV, LVESV, RVEDV and RVESV were −3.92 mL, −3.72 mL, 30.21 mL and 8.06 mL, respectively.

Segmentation Performance for U-Net with Nearest-Neighbor Down-Sampling

Simulations were carried out on the images that were down-sampled using nearest-neighbor method. The average Dice metric, Jaccard index, Hausdorff distance, mean contour distance, and $R_{vol}^2$ for U-Net and U-Net-SAD computed based on the ground-truth are reported in Table 3.

The Dice metrics for U-Net method were 84.50%, 79.42%, 77.68% and 71.33% for LVED, LVES, RVED and RVES, respectively. The corresponding Dice metrics for U-Net-SAD method were 87.08%, 82.27%, 81.83% and 74.79%, respectively. Sensitivity, specificity, PPV and NPV for U-Net and U-Net-SAD are summarized in Table 4. The absolute and relative difference between predicted and ground-truth volumes for LV and RV chambers at ED and ES as well as SV and EF are summarized in the last two columns of the Table 5. The correlation and Bland-Altman plots for U-Net-SAD are shown by red dots in FIGS. 7A to 10D. The bias values of the U-Net for LVEDV, LVESV, RVEDV and RVESV were 7.18 mL, 4.16 mL, 8.42 mL and 5.38 mL, respectively. The corresponding bias values of U-Net-SAD for LVEDV, LVESV, RVEDV and RVESV were 3.58 mL, 2.83 mL, 6.96 mL, and 4.51 mL, respectively.

Segmentation Performance for U-Net with Bi-Cubical Down-Sampling

Using the images that were down-sampled according to the bi-cubical method, the average Dice metric, Jaccard index, relative volume difference and $R_{vol}^2$ for U-Net and U-Net-SAD calculated based on the ground-truth are reported in Table 7.

TABLE 7

Different quantitative metrics for models trained on
bi-cubically down-sampled data

|  | Dice (%) | Jaccard (%) | Rel. volume difference (%) | R2vol (%) | t-test p-value |
|---|---|---|---|---|---|
| LVED | | | | | |
| FCN | 88.46 (18.44) | 82.59 (20.27) | 6.03 (10.31) | 98.54 | 0.0147 |
| FCN-SAD | 91.03 (14.94) | 85.82 (17.04) | 4.58 (6.06) | 99.24 | 0.2739 |
| U-Net | 85.53 (22.97) | 79.46 (24.04) | 10.66 (17.67) | 89.79 | 4.755e-3 |
| U-Net-SAD | 87.38 (21.13) | 81.71 (22.29) | 8.26 (15.90) | 97.70 | 0.443e-3 |
| LVES | | | | | |
| FCN | 83.10 (22.61) | 75.61 (23.80) | 10.07 (9.31) | 95.70 | 0.0786 |
| FCN-SAD | 86.82 (16.45) | 79.40 (18.88) | 7.87 (5.08) | 97.84 | 0.0945 |
| U-Net | 81.61 (22.56) | 73.38 (23.84) | 23.35 (39.89) | 79.12 | 9.913e-4 |
| U-Net-SAD | 83.90 (20.72) | 76.10 (21.96) | 15.56 (26.95) | 93.28 | 3.786e-4 |
| RVED | | | | | |
| FCN | 80.93 (22.90) | 72.57 (24.30) | 9.28 (14.24) | 87.71 | 0.0159 |
| FCN-SAD | 84.70 (18.79) | 76.78 (20.76) | 6.77 (8.63) | 94.85 | 0.0858 |
| U-Net | 76.54 (29.45) | 68.97 (29.59) | 12.40 (17.90) | 81.75 | 0.0134 |
| U-Net-SAD | 81.75 (22.79) | 73.76 (24.43) | 9.69 (12.38) | 91.79 | 0.0251 |
| RVES | | | | | |
| FCN | 77.23 (22.84) | 67.22 (23.63) | 13.55 (15.58) | 90.55 | 0.0226 |
| FCN-SAD | 80.57 (19.71) | 70.90 (21.20) | 11.02 (13.75) | 92.85 | 0.6585 |
| U-Net | 70.24 (30.35) | 60.91 (29.44) | 18.54 (19.88) | 82.60 | 0.151e-3 |
| U-Net-SAD | 74.81 (25.50) | 64.89 (25.62) | 13.75 (15.44) | 88.05 | 1.783e-3 |

The Dice metrics for U-Net method were 85.53%, 81.61%, 76.54% and 70.24% for LVED, LVES, RVED and RVES, respectively. The corresponding Dice metrics for U-Net-SAD method were 87.38%, 83.90%, 81.75%, and 74.81%, respectively.

Segmentation Performance for FCN-2.0 and FCN-SAD-2.0

To avoid conflict with the definition of HD, MCD, etc., CMR images with no ground-truth segmentation contours are removed from the test set. The average Dice metric, Jaccard index, Hausdorff and mean contour distance for FCN-2.0 and FCN-SAD-2.0 are reported in Table 8. The Dice metrics for FCN-2.0 were 86.66%, 82.79%, 80.84% and 72.38% for LVED, LVES, RVED and RVES, respectively. The corresponding Dice metrics for FCN-SAD-2.0 were 91.28%, 86.74%, 84.52% and 77.02% for LVED, LVES, RVED and RVES, respectively.

TABLE 8

Mean (SD) of different quantitative metrics for nearest-neighbor
down-sampling (CHD + ACDC datasets)

|  | Dice (%) | Jaccard (%) | HD (mm) | MCD (mm) |
|---|---|---|---|---|
| LVED | | | | |
| FCN-2.0 | 86.66 (22.68) | 81.11 (23.65) | 7.06 (13.01) | 3.06 (10.39) |
| FCN-SAD-2.0 | 91.28 (15.08) | 86.21 (16.55) | 5.16 (9.11) | 2.00 (7.82) |
| LVES | | | | |
| FCN-2.0 | 82.79 (23.06) | 75.31 (24.20) | 8.25 (17.78) | 3.6 (12.36) |
| FCN-SAD-2.0 | 86.74 (17.64) | 79.58 (19.63) | 6.00 (10.85) | 2.71 (9.99) |
| RVED | | | | |
| FCN-2.0 | 80.84 (22.65) | 72.33 (24.00) | 14.28 (18.93) | 5.78 (14.66) |
| FCN-SAD-2.0 | 84.52 (18.78) | 76.48 (20.64) | 12.07 (16.02) | 4.18 (9.06) |
| RVES | | | | |
| FCN-2.0 | 72.38 (26.83) | 62.20 (26.47) | 15.77 (21.33) | 7.42 (17.86) |
| FCN-SAD-2.0 | 77.02 (22.83) | 66.94 (23.66) | 13.41 (16.43) | 4.59 (8.56) |

Many challenges currently exist for segmenting cardiac chambers from CMR images, notably in pediatric and CHD patients. In the past few years, a great deal of activities has been witnessed in the learning-based approaches to CMR segmentation. Despite their relative successes, they still have certain limitations. Small datasets incur a large bias to the segmentation, which makes these methods unreliable when the heart shape is outside the learning set (e.g., CHDs and post-surgically remodeled hearts). In brief, in pediatric cardiac imaging, learning-based methods are less than optimal with respect to predictive performance and remain computationally difficult, due to the complexity of estimating parameters, and their convergence is not guaranteed.

While current methods using deep-learning, e.g., VGG-16 network and U-Net, achieve good results for subjects with relatively normal structure, they are not as reliable for segmenting the CMR images of CHD patients. The main reason for this shortcoming is the lack of a large database that includes CMR studies from CHD subjects, as they are highly heterogeneous.

Current software platforms designed for adult patients, for example, cvi42 by Circle Cardiovascular Imaging Inc, was previously reported to have many shortcomings when used for pediatric or CHD applications. Children are not just little adults; pediatric patient characteristics, such as cardiac anatomy, function, higher heart rates, degree of cooperativity, and smaller body size, all affect post-processing approaches to CMR, and there is currently no CMR segmentation tool dedicated to pediatric patients. Current clinically-available segmentation tools cannot be realistically used for children.

Synthetic CMR and the corresponding segmented images can be generated to address this shortcoming. As reported in Table 5, cvi42's rendered volumes led to a significant difference between the predicted and true values of volumetric measures although it uses the original high quality and high resolution CMR images coming from the scanner for its predictions. Synthetic data augmentation also improved volume prediction for the U-Net. In addition, as shown in Table 5, FCN-SAD method outperforms U-Net-SAD for both chambers at end-systole and end-diastole. As reported in Table 7, the FCN-SAD passed the t-test's null hypothesis that the predicted and ground-truth volumes have identical expected values for LVED, LVES, RVED and RVES. However, cvi42 only passed the t-test for LVED. Since the p-value is largely affected by the sample size etc., the ICC values are also reported for all models in Table 6. The FCN and FCN-SAD models led to an excellent correlation coefficient for both LV and RV at ED and ES. U-Net-SAD also resulted in ICC values greater than 0.90; however, U-Net failed to achieve the excellent threshold for LVES. All cvi42's ICC values are below the excellent threshold as well. Although the exact deep learning architecture of cvi42 is not known, the main reason for the relatively poor performance of cvi42 on pediatric CHD patients is probably the training of its neural network on the UK Biobank, which is limited to the adult CMR images. More precisely, UK Biobank dataset does not represent features that are inherent to the heart of children with CHD.

As indicated in Tables 3 and 4, the disclosed techniques outperform cvi42 in Dice metric, Jaccard indices, HD, MCD, volume correlation, sensitivity, specificity, Positive predictive value (PPV) and Negative predictive value (NPV) as well. For LV segmentation, FCN-SAD improved Dice metric from 73.17% to 90.63% and from 70.98% to 84.96% over cvi42 at end-diastolic and end-systolic phases, respectively. Similar improvement was observed for RV segmentation where Dice metric was improved from 54.29% to 84.44% and from 53.70% to 79.22% at end-diastolic and end-systolic phases, respectively. FCN-SAD also reduced the average Hausdorff and mean contour distances compared to cvi42. This improved alignment between the contours was observed for both LV and RV at both end-diastolic and end-systolic phases. Similar improvement was observed for FCN-SAD over U-Net-SAD. For LV segmentation, FCN-SAD improved the Dice metric over U-Net-SAD from 87.08% to 90.63% for ED, and from 82.27% to 84.96% for ES. Similarly, FCN-SAD improved U-Net-SAD for RV segmentation from 81.83% to 84.44% for ED, and from 74.79% to 79.22% for ES. FCN-SAD also led to lower HD and MCD values compared to the U-Net-SAD method. The data augmentation using DCGAN improved the Dice metric values by about 3%. Improvement was observed for Jaccard indices, HD, MCD, volume correlation, sensitivity, specificity, PPV and NPV as well.

As shown in Table 3, synthetic data augmentation improved both Dice and Jaccard indices by about 3% for U-Net, which shows that synthetic data augmentation can improve the performance of FCN methods regardless of the type. Compared to the U-Net method, similar improvement was observed in U-Net-SAD for both HD and MCD as well. Table 3 reveals that the FCN method outperforms U-Net. Similarly, the FCN-SAD method outperforms U-Net-SAD in all metrics for LVED, LVES, RVED and RVES. Synthetic data augmentation also improved both Dice and Jaccard indices by about 4% for FCN-2.0. Similar improvement was observed in FCN-SAD-2.0 for both HD and MCD, which indicates better alignment between predicted and manual segmentation contours.

As expected, RV segmentation proved to be more challenging than LV segmentation due to the complex shape and anatomy of the RV chamber. The sophisticated crescent shape of RV as well as the considerable variations among the subjects make it harder for the segmentation model to learn the mapping from a CMR image to its corresponding mask. Another major limiting factor that affects the performance of RV segmentation is the similarity of the signal intensities for RV trabeculations and myocardium.

The disclosed techniques have overcome these limiting issues by learning the generative process through which each RV chamber is segmented. This information is then passed to the segmentation model via synthetic samples obtained from that generative process.

Larger contours can be more precisely delineated compared to the smaller ones. Segmentation of the CMR slices near the apex, particularly at the end-systole, is more challenging due to their small and irregular shape. Table I shows that both Dice and Jaccard indices are higher at end-diastole versus end-systole for both ventricles. Another possible reason for lower performance at end-systole can be attributed to their small mask area and the smaller values of denominator at Eq. (3), which can lead to a major effect on the final values of these metrics, in case of even a few misclassified pixels.

Figure 8A:
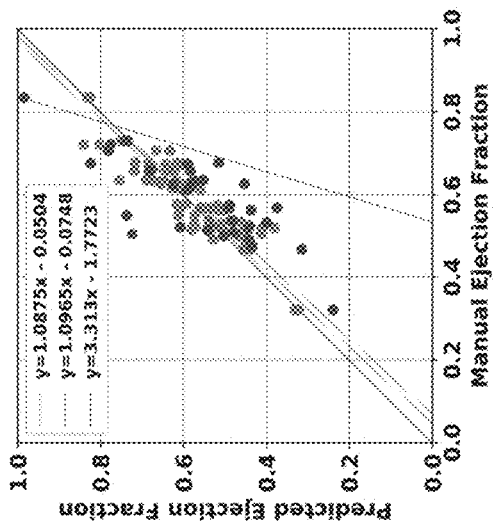
FIG. 8A illustrates an example correlation plot for nearest-neighbor down-sampling.
Figure 8B:
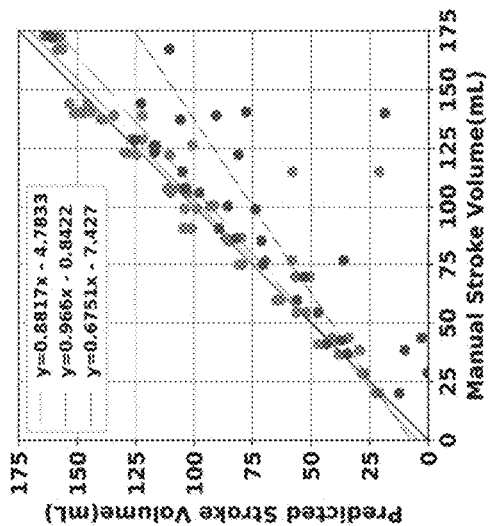
FIG. 8B illustrates another example correlation plot for nearest-neighbor down-sampling.
Figure 8C:
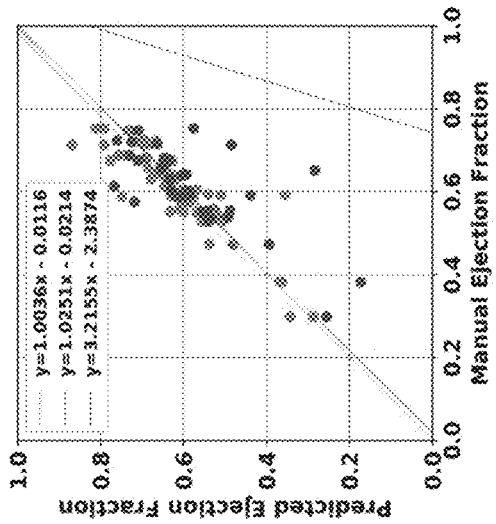
FIG. 8C illustrates another example correlation plot for nearest-neighbor down-sampling.
Figure 8D:
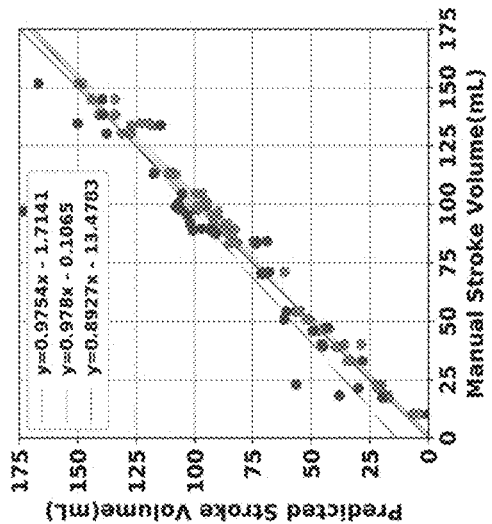
FIG. 8D illustrates yet another example correlation plot for nearest-neighbor down-sampling.
Figure 11A:
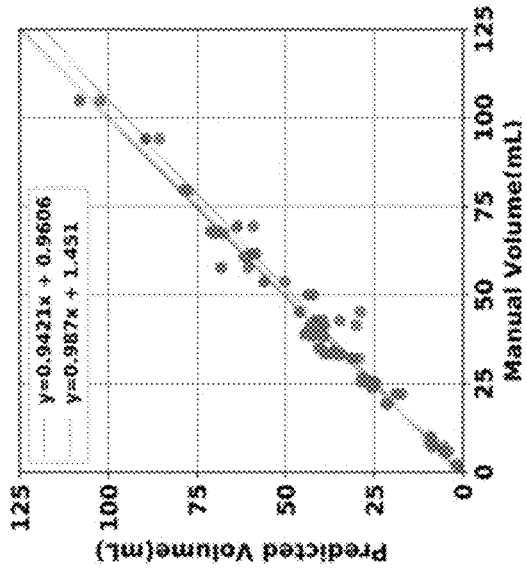
FIG. 11A illustrates an example correlation plot for bi-cubical down-sampling.
Figure 11B:
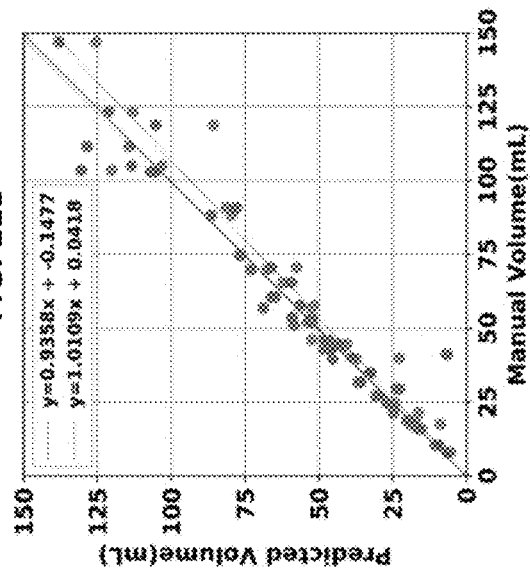
FIG. 11B illustrates another example correlation plot for bi-cubical down-sampling.
Figure 11C:
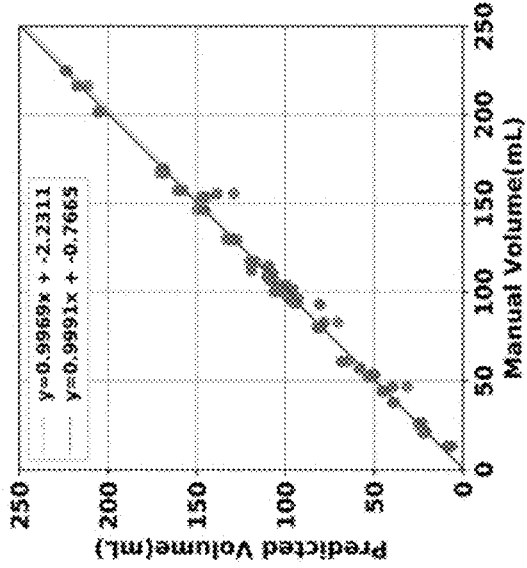
FIG. 11C illustrates another example correlation plot for bi-cubical down-sampling.
Figure 11D:
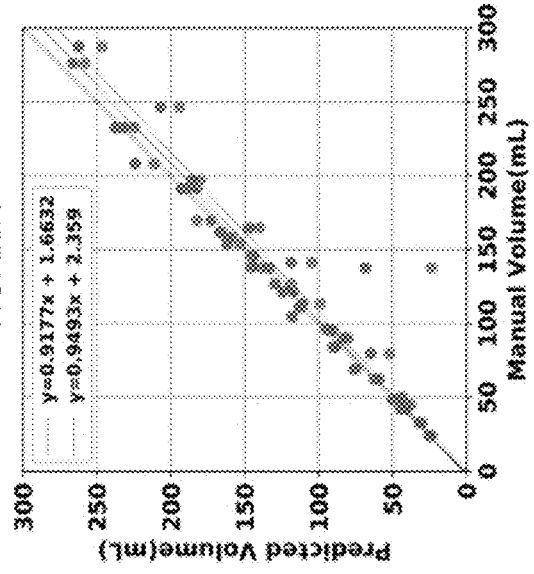
FIG. 11D illustrates yet another example correlation plot for bi-cubical down-sampling.
Figure 13A:
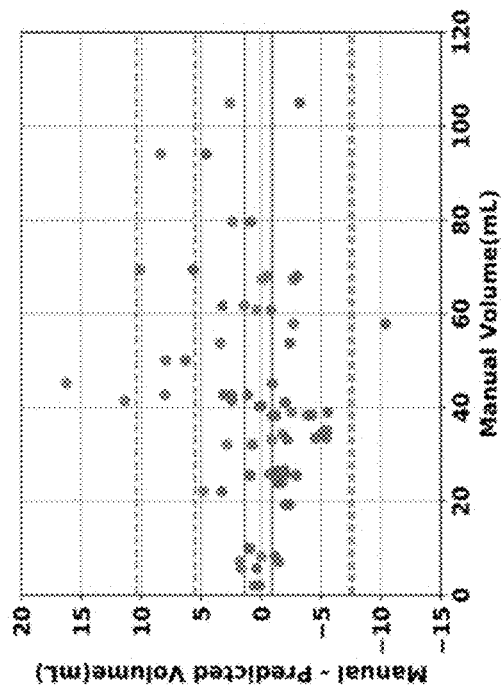
FIG. 13A illustrate an example Bland-Altman plot for bi-cubical down-sampling.
Figure 13B:
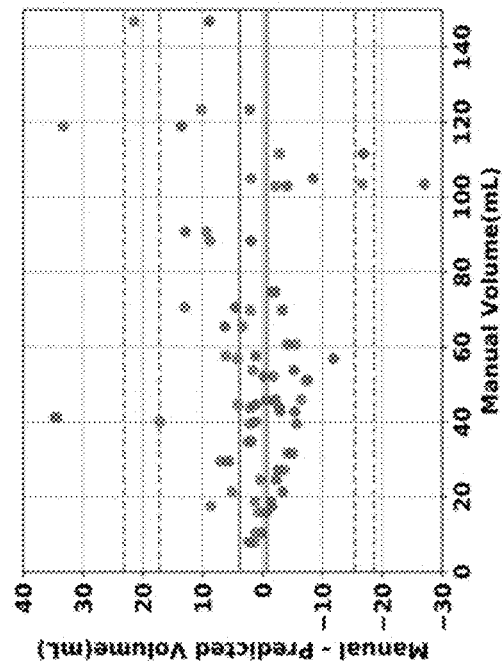
FIG. 13B illustrate another example Bland-Altman plot for bi-cubical down-sampling.
Figure 13C:
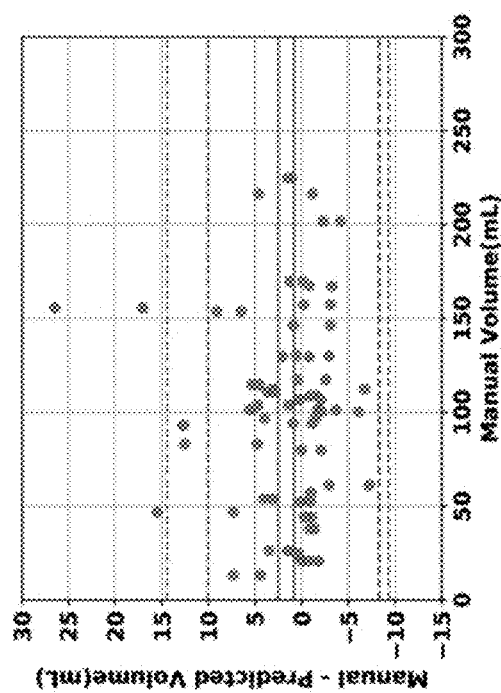
FIG. 13C illustrate another example Bland-Altman plot for bi-cubical down-sampling.
Figure 13D:
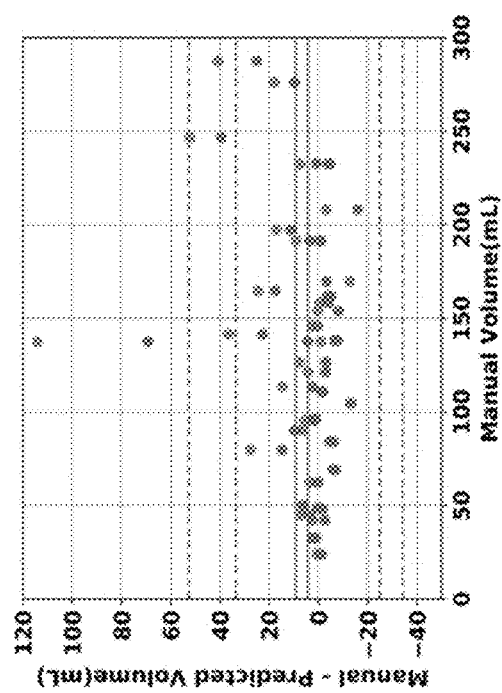
FIG. 13D illustrate yet another example Bland-Altman plot for bi-cubical down-sampling.
Figure 14A:
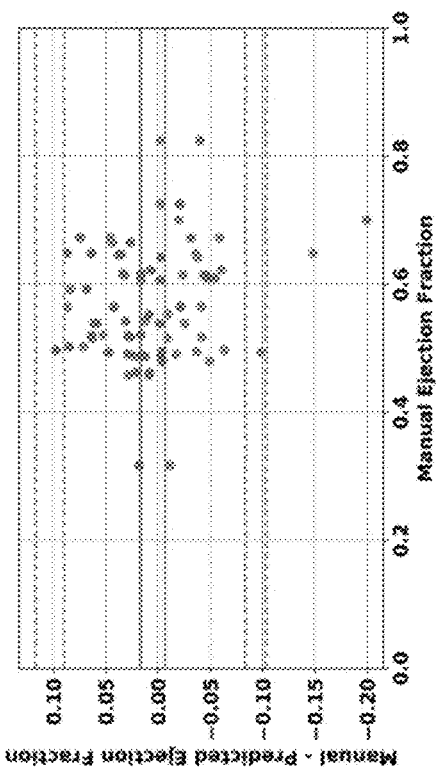
FIG. 14A illustrates an example Bland-Altman plot for bi-cubical down-sampling.
Figure 14B:
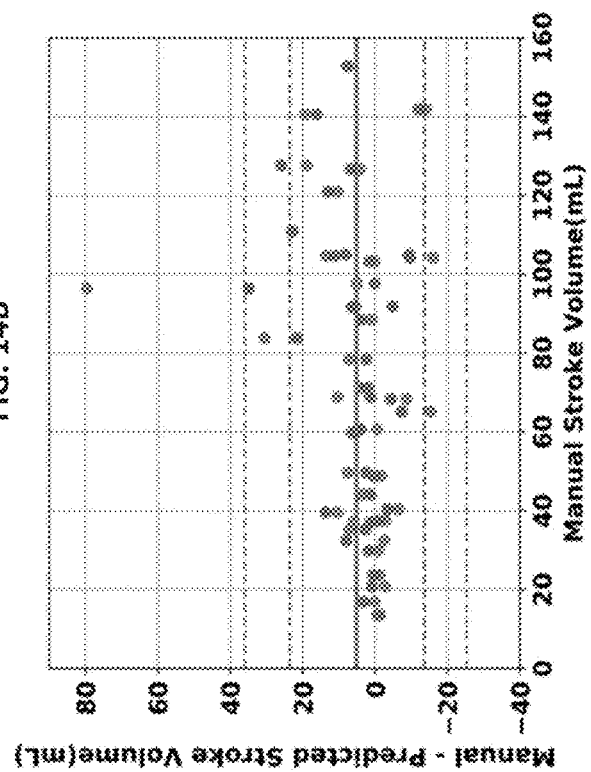
FIG. 14B illustrates another example Bland-Altman plot for bi-cubical down-sampling.
Figure 14C:
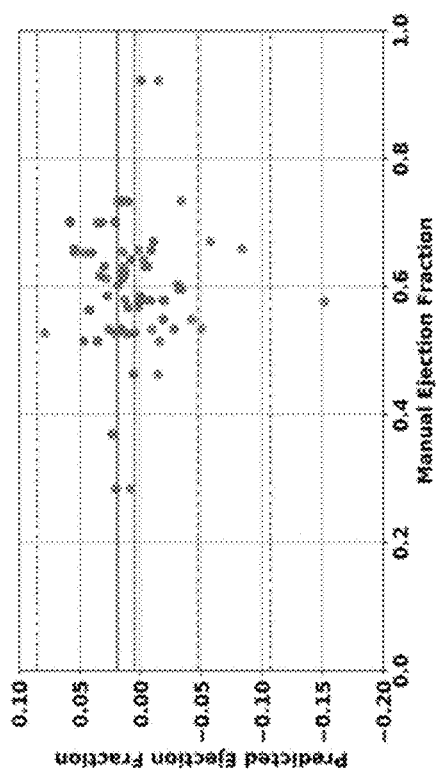
FIG. 14C illustrates another example Bland-Altman plot for bi-cubical down-sampling.
Figure 14D:
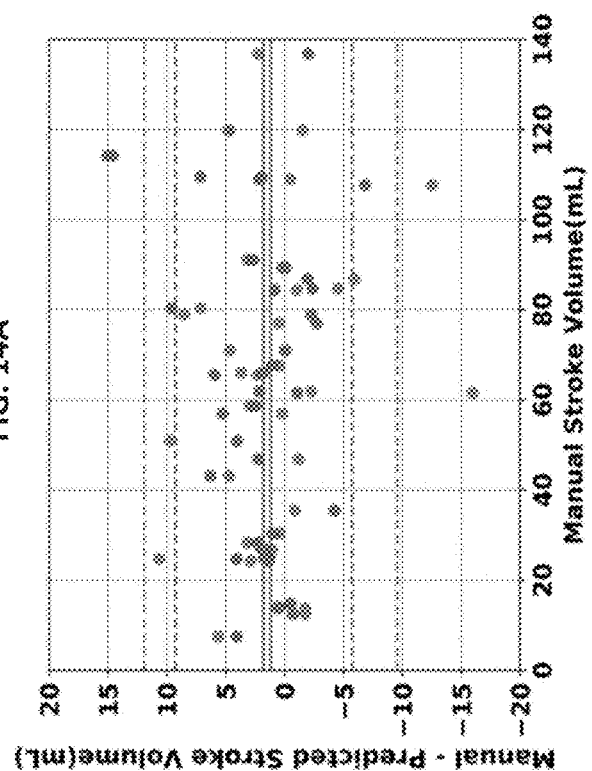
FIG. 14D illustrates yet another example Bland-Altman plot for bi-cubical down-sampling.

FIGS. 7A and 7B show that the results generated by the disclosed FCN-SAD model leads to high correlation for LVEDV and LVESV. This in turn leads to high correlation in EF and SV as shown in FIGS. 8A and 8C in addition to $R_{vol}^2$ values in Table I. Similarly, a high correlation was observed for RVEDV and RVESV in FIGS. 7C and 7D, which subsequently leads to high correlation in EF and SV as shown in FIGS. 8B-8D as well as the $R_{vol}^2$ scores in Table I. Bland-Altman analyses in FIGS. 8A to 10D show negligible bias for the results due to FCN-SAD model trained on the synthetically augmented data.

The average elapsed times to segment a typical image in a graphics processing unit (GPU)-accelerated computing platform is 10 ms. Overall, an example model takes 0.1 s to process each patient's CMR data. Simulations show that even on a central processing unit (CPU)-based computing platform, the disclosed techniques require about 1.3 s to segment each patient's CMR images, which indicates the clinical applicability of the disclosed automated segmentation model. Similar quantitative and volumetric results were observed when the whole training and validation procedures were repeated with a different random split of training and test subjects. This indicates that no noticeable bias has occurred by the way subjects are categorized into training and test set.

The significance of the choice of down-sampling method on the segmentation performance needs to be noted. The entire process of training and testing using both nearest-neighbor and bi-cubic down-sampling methods can be repeated multiple times. Compared to the nearest-neighbor down-sampling method, the bi-cubic down-sampling provides a better performance. For example, the bi-cubic FCN-SAD results passed the t-test denoting the predicted and ground-truth volumes have identical expected value for LVED while the nearest-neighbor FCN-SAD did not. The main reason behind the superior performance of the bi-cubic down-sampling method is its larger mask area compared to the nearest-neighbor method.

Manual segmentation is subjective, less reproducible, expensive, time consuming and requires dedicated experts. Therefore, fully automated and accurate segmentation methods are desirable to provide precise clinical indices such as ejection fraction, chamber volume, etc. in a timely manner. The disclosed learning-based framework provides an automated, fast and accurate model for LV and RV segmentation in children with complex congenital heart disease and has the potential to be used across the entire cardiac cycle.

The disclosed techniques can be implemented as a fully convolutional network for an automatic endocardial segmentation of left and right ventricles from CMR images of patients with complex congenital heart disease. Contrary to many existing automated approaches, the disclosed framework does not make any assumption about the image or the structure of the heart and performs the segmentation by learning features of the image at different levels of abstraction in the hierarchy of network layers. To improve the robustness and accuracy of our segmentation method, a generative adversarial network can be used to enlarge the training data via synthetically generated and realistic looking samples. The fully convolutional network trained on both real and synthetic data exhibits an improvement in various statistical and clinical measures such as Dice, Hausdorff distance and volume over the test set.

Figure 15:
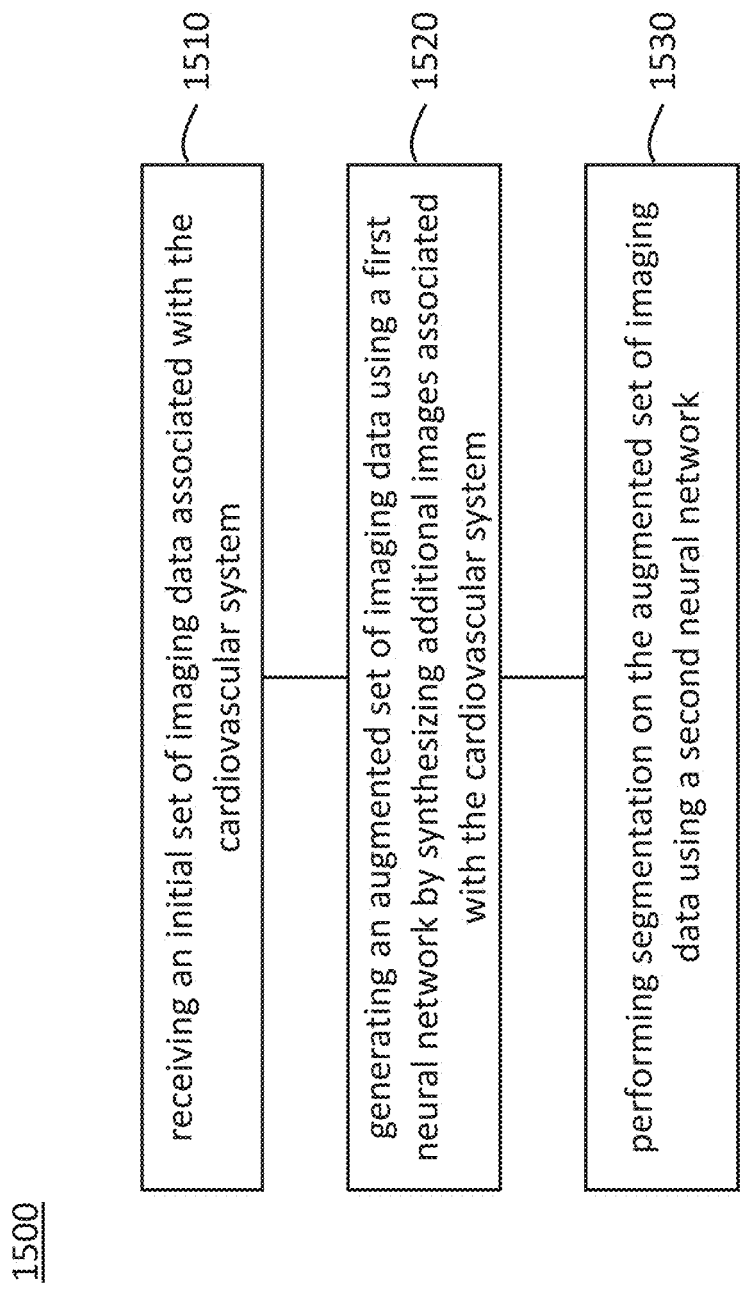
FIG. 15 illustrates an example method performing automatic segmentation of image data associated with cardiovascular system that can include the whole heart or parts thereof in accordance with one or more embodiments of the present technology.

FIG. 15 illustrates an example method 1500 for performing automatic segmentation of image data associated with cardiovascular system that can include the whole heart or parts thereof in accordance with one or more embodiments of the present technology. The method 1500 includes, at operation 1510, receiving an initial set of image data associated with the cardiovascular system. The method 1500 includes, at operation 1520, generating an augmented set of image data using a first neural network by synthesizing additional images associated with the cardiovascular system. The method 1500 also includes, at operation 1530, performing segmentation on the augmented set of image data using a second neural network.

In some embodiments, the first neural network comprises a deep convolutional generative adversarial network. In some embodiments, training of the deep convolutional generative adversarial network comprises, in each of multiple training steps performed iteratively: tuning a discriminator of the deep convolutional generative adversarial network while a generator of the deep convolutional generative adversarial network remains unchanged, and training the generator of the deep convolutional generative adversarial network while the discriminator of the deep convolutional generative adversarial network remains unchanged. In some embodiments, the training of the deep convolutional generative adversarial network completes upon an equilibrium being established between the discriminator and the generator.

In some embodiments, the initial set of image data includes one or more of: magnetic resonance image data, echocardiography data, or computed tomography (CT) image data. In some embodiments, the initial set of image data is associated with pediatric congenital heart diseases. In some embodiments, the augmented set of image data synthesized by the first neural network includes synthesized image data other than images produced by affine transformations. In some embodiments, the augmented set of image data synthesized by the first neural network includes three-dimensional image data. In some embodiments, the first neural network is used for synthesizing data associated with a heart's left ventricle. The method also includes using an additional neural network for synthesizing additional image data associated with one or more of: the heart's right ventricle, right atrium or left atrium.

Figure 16:
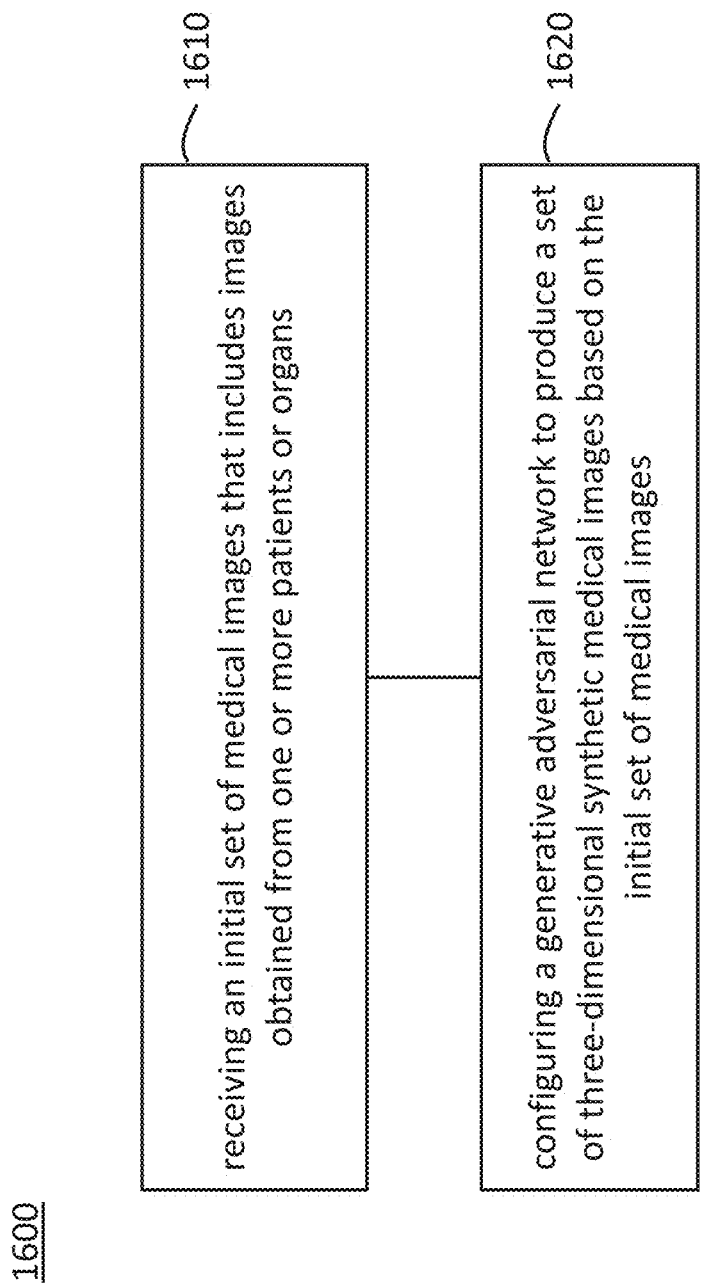
FIG. 16 illustrates an example method for generating medical images in accordance with one or more embodiments of the present technology.

FIG. 16 illustrates an example method 1600 for generating medical images in accordance with one or more embodiments of the present technology. The method 1600 includes, at operation 1610, receiving an initial set of medical images. The initial set of medical images includes images obtained from one or more patients or organs, for example, two-dimensional images associated with the one or more patients or organs. The method 1600 also includes, at operation 1620, configuring a generative adversarial network to produce a set of three-dimensional synthetic medical images based on the initial set of medical images. The generative adversarial network comprises a discriminator and a generator. The generative adversarial network is iteratively trained until an equilibrium is established between the discriminator and the generator.

In some embodiments, the method includes configuring the generative adversarial network as a three-dimensional (3D) deep convolutional generative adversarial network to generate the set of three-dimensional synthetic medical images. In some embodiments, the set of three-dimensional synthetic medical images resemble real magnetic resonance images associated with the one or more patients or organs and is usable for processing by an additional neural network.

Figure 17:
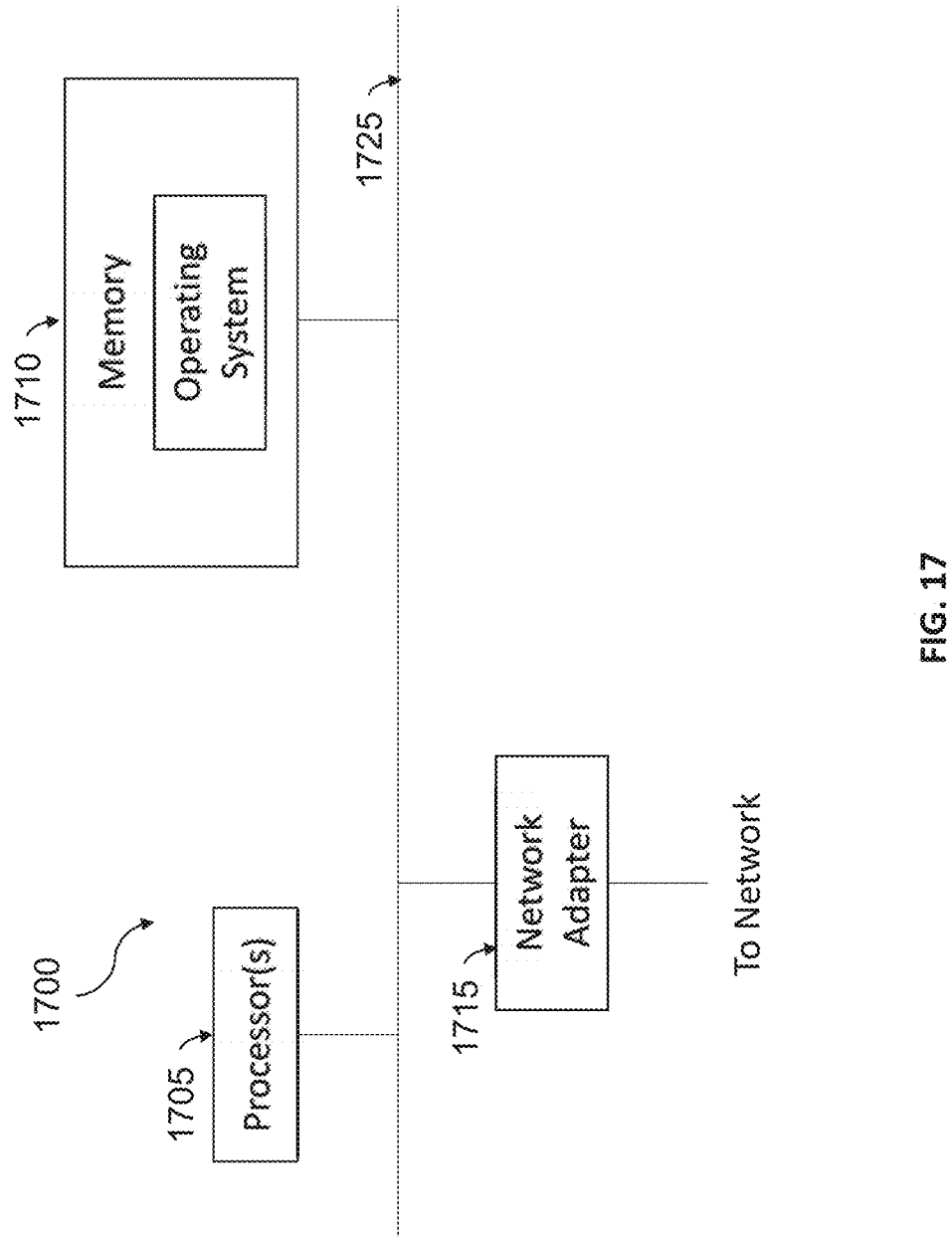
FIG. 17 is a block diagram illustrating an example of the architecture for a computer system or other control device that can be utilized to implement various portions of the presently disclosed technology.

FIG. 17 is a block diagram illustrating an example of the architecture for a computer system or other control device 1700 that can be utilized to implement various portions of the presently disclosed technology (e.g., various types of neural networks). In FIG. 17, the computer system 1700 includes one or more processors 1705 and memory 1710 connected via an interconnect 1725. The interconnect 1725 may represent any one or more separate physical buses, point to point connections, or both, connected by appropriate bridges, adapters, or controllers. The interconnect 1725, therefore, may include, for example, a system bus, a Peripheral Component Interconnect (PCI) bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 674 bus, sometimes referred to as "Firewire."

The processor(s) 1705 may include central processing units (CPUs), graphics processing units (GPUs), or other types of processing units (such as tensor processing units) to control the overall operation of, for example, the host computer. In certain embodiments, the processor(s) 1705 accomplish this by executing software or firmware stored in memory 1710. The processor(s) 1705 may be, or may include, one or more programmable general-purpose or special-purpose microprocessors, digital signal processors (DSPs), programmable controllers, application specific integrated circuits (ASICs), programmable logic devices (PLDs), or the like, or a combination of such devices.

The memory 1710 can be or include the main memory of the computer system. The memory 1710 represents any suitable form of random access memory (RAM), read-only memory (ROM), flash memory, or the like, or a combination of such devices. In use, the memory 1710 may contain, among other things, a set of machine instructions which, when executed by processor 1705, causes the processor 1705 to perform operations to implement embodiments of the presently disclosed technology.

Also connected to the processor(s) 1705 through the interconnect 1725 is a (optional) network adapter 1715. The network adapter 1715 provides the computer system 1700 with the ability to communicate with remote devices, such as the storage clients, and/or other storage servers, and may be, for example, an Ethernet adapter or Fiber Channel adapter.

Figure 18:
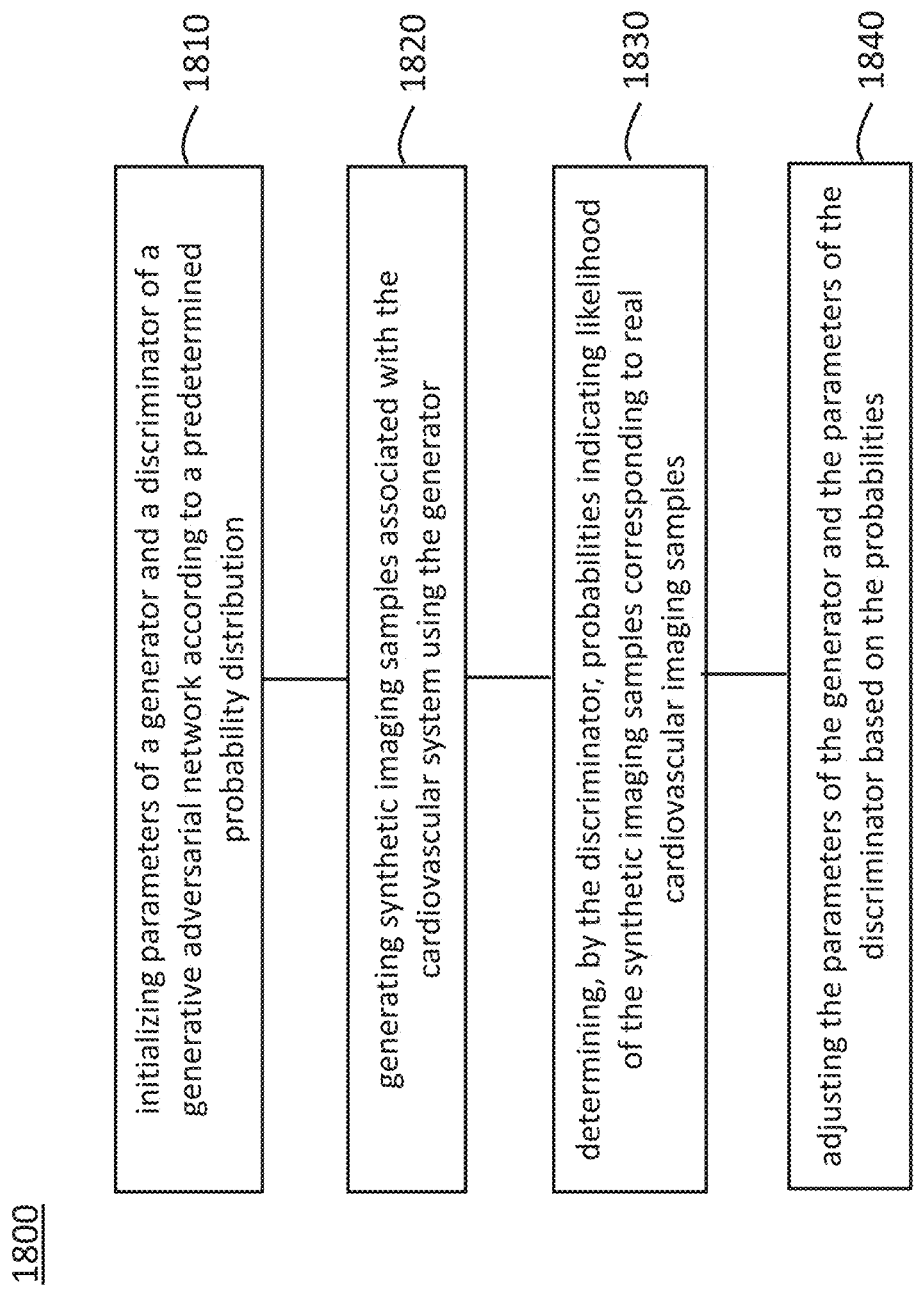
FIG. 18 illustrates an example method for generating synthetic image data associated with a cardiovascular system in accordance with one or more embodiments of the present technology.

FIG. 18 illustrates an example method 1800 for generating synthetic image data associated with a cardiovascular system in accordance with one or more embodiments of the present technology. The method 1800 includes, at operation 1810, initializing parameters of a generator and a discriminator of a generative adversarial network according to a predetermined probability distribution. The method 1800 includes, at operation 1820, generating synthetic medical images associated with the cardiovascular system using the generator. The method 1800 includes, at operation 1830, determining, by the discriminator, probabilities indicating likelihood of the synthetic medical images corresponding to real cardiovascular images acquired from an individual (e.g., a patient or a test subject). The method 1800 also includes, at operation 1840, adjusting the parameters of the generator and the parameters of the discriminator based on the probabilities determined by the discriminator to the generator and to the discriminator to allow the parameters of the generator and the parameters of the discriminator to be adjusted in an iterative process until an equilibrium between the generator and the discriminator is established. In the iterative process, the parameters of the generator remain unchanged when the parameters of the discriminator are adjusted, and the parameters of the discriminator remain unchanged when the parameters of the generator are adjusted.

In some embodiments, adjusting the parameters of the generator and the parameters of the discriminator of the generative adversarial network includes: adjusting the parameters of the discriminator using a first set of imaging samples labeled designated as real cardiovascular samples of a person and a second set of imaging samples labeled designated as synthetic samples generated by a computer system, and adjusting the parameters of the generator using a third set of synthetic imaging samples designated labeled as real cardiovascular samples. In some embodiments, the method further includes segmenting the synthetic imaging samples using the generator of the generative adversarial network. In some embodiments, the method further includes segmenting the synthetic imaging samples using a fully connected neural network.

In some embodiments, the predetermined probability distribution consists of comprises a Gaussian distribution. In some embodiments, the synthetic medical images include three-dimensional image data. In some embodiments, the synthetic medical images are associated with a congenital heart disease. The synthetic imaging samples include one or more of: magnetic resonance image data, echocardiography data, or computed tomography (CT) image data.

In some embodiments, the generative adversarial network is configured to synthesize data associated with a heart and the segmentation of one of the heart's left ventricle, the heart's right ventricle, the heart's left atrium, or the heart's right atrium. In some embodiments, the generative adversarial network is configured to synthesize data associated with a heart and the segmentation of more than one heart chambers. The hear chambers can be a heart's left ventricle, a heart's right ventricle, a heart's left atrium, or a heart's right atrium. That is, the generative adversarial network is configured to synthesize data associated with a heart and segmentation of one or more of the heart's chambers, including the heart's left ventricle, the heart's right ventricle, the heart's left atrium, or the heart's right atrium.

At least parts of the disclosed embodiments (e.g., the neural networks) can be implemented in digital electronic circuitry, or in computer software, firmware, or hardware. For example, electronic circuits can be used to control the operation of the detector arrays and/or to process electronic signals that are produced by the detectors. At least some of those embodiments or operations can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Computer-readable media suitable for storing computer program instructions and data include all forms of non-volatile memory, media and memory devices, including, by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A generative adversarial network stored on a non-transitory computer readable medium, comprising:

a generator configured to generate synthetic medical image data attributed to a cardiovascular system and segmentation masks corresponding to the synthetic medical image data, the generator having parameters that have been initialized according to a predetermined probability distribution; and a discriminator configured to receive the synthetic medical image data from the generator and determine probabilities indicating likelihood of the synthetic medical image data corresponding to real cardiovascular images acquired from an individual, the discriminator having parameters that have been initialized according to the predetermined probability distribution, wherein the discriminator is further configured to provide the probabilities determined by the discriminator to: (1) the generator and (2) an input of the discriminator to allow the parameters of the generator and the parameters of the discriminator to be iteratively adjusted until an equilibrium between the generator and the discriminator is established, wherein the generator is configured to output two channels comprising a first channel that outputs information representing the synthetic medical image data and a second channel that outputs information representing the segmentation masks corresponding to the synthetic medical image data.

2. The generative adversarial network of claim 1, wherein the predetermined probability distribution consists of a Gaussian distribution.

3. The generative adversarial network of claim 2, wherein the parameters of the generator and the parameters of the discriminator are initialized with a zero mean value.

4. The generative adversarial network of claim 1, configured to adjust the parameters of the generator and the parameters of the discriminator based on:

adjusting the parameters of the discriminator based on a first set of probabilities generated by the discriminator, wherein the first set of probabilities are generated using a first set of image samples designated as real cardiovascular samples acquired from an individual and a second set of image samples designated as synthetic samples generated by a computer system; and adjusting the parameters of the generator based on a second set of probabilities generated by the discriminator, wherein the second set of probabilities are generated using a third set of synthetic image samples designated as real cardiovascular samples.

5. The generative adversarial network of claim 4, wherein the parameters of the generator remain unchanged when the parameters of the discriminator are adjusted, and wherein the parameters of the discriminator remain unchanged when the parameters of the generator are adjusted.

6. The generative adversarial network of claim 1, wherein the generative adversarial network is part of a neural network system, wherein the neural network system is configured to receive an initial set of image data and provide an augmented set of image data using the synthetic medical image data generated by the generative adversarial network, the neural network system further comprising an additional neural network configured to perform segmentation on another set of image data.

7. The generative adversarial network of claim 6, wherein the additional neural network comprises a fully convolutional neural network.

8. The generative adversarial network of claim 6, wherein the initial set of image data is associated with a congenital heart disease, the initial set of image data including one or more of: magnetic resonance image data, echocardiography data, or computed tomography (CT) image data.

9. The generative adversarial network of claim 6, wherein the initial set of image data includes two-dimensional image data, and wherein the augmented set of image data includes three-dimensional image data generated based on the two-dimensional image data.

10. The generative adversarial network of claim 6, wherein the generative adversarial network is configured to synthesize data associated with a heart and segmentation of one or more of the heart's chambers, wherein the chambers comprise the heart's left ventricle, the heart's right ventricle, the heart's left atrium, or the heart's right atrium.

11. A computer-implemented method for generating synthetic image data associated with a cardiovascular system, comprising:

initializing parameters of a generator and a discriminator of a generative adversarial network according to a predetermined probability distribution;

generating, by the generator, synthetic image samples associated with the cardiovascular system and segmentation masks corresponding to the synthetic image samples, determining, by the discriminator, probabilities indicating likelihood of the synthetic image samples corresponding to real cardiovascular images acquired from an individual; and adjusting the parameters of the generator and the parameters of the discriminator based on the probabilities determined by the discriminator in an iterative process until an equilibrium between the generator and the discriminator is established, wherein, in the iterative process, the parameters of the generator remain unchanged when the parameters of the discriminator are adjusted and the parameters of the discriminator remain unchanged when the parameters of the generator are adjusted.

12. The computer-implemented method of claim 11, wherein adjusting the parameters of the generator and the parameters of the discriminator of the generative adversarial network includes:

adjusting the parameters of the discriminator using a first set of image samples designated as real cardiovascular samples acquired from an individual and a second set of image samples designated as synthetic samples generated by a computer system; and adjusting the parameters of the generator using a third set of synthetic image samples designated as real cardiovascular image samples acquired from an individual.

13. The computer-implemented method of claim 11, further comprising:

segmenting the synthetic image samples using the generator of the generative adversarial network.

14. The computer-implemented method of claim 11, further comprising:

segmenting the synthetic image samples using a fully connected neural network.

15. The computer-implemented method of claim 11, wherein the predetermined probability distribution consists of a Gaussian distribution.

16. The computer-implemented method of claim 11, wherein the synthetic image samples include three-dimensional image data.

17. The computer-implemented method of claim 11, wherein the synthetic image samples are associated with a congenital heart disease, the synthetic image samples including one or more of: magnetic resonance image data, echocardiography data, or computed tomography (CT) image data.

18. The computer-implemented method of claim 11, wherein the generative adversarial network is configured to synthesize data associated with a heart and segmentation of one or more of the heart's chambers, wherein the chambers comprise the heart's left ventricle, the heart's right ventricle, the heart's left atrium, or the heart's right atrium.

19. A non-transitory computer readable medium having code stored thereon, wherein the code, when executed by a processor, causes the processor to implement a method that comprises:
   initializing parameters of a generator and a discriminator of a generative adversarial network according to a predetermined probability distribution;
   generating, by the generator, synthetic medical images attributed to cardiovascular system and segmentation masks corresponding to the synthetic medical images using the generator,
   determining, by the discriminator, probabilities indicating likelihood of the synthetic medical images corresponding to real cardiovascular image samples acquired from an individual; and
   adjusting the parameters of the generator and the parameters of the discriminator based on the probabilities determined by the discriminator in an iterative process until an equilibrium between the generator and the discriminator is established,
   wherein, in the iterative process the parameters of the generator remain unchanged when the parameters of the discriminator are adjusted, and the parameters of the discriminator remain unchanged when the parameters of the generator are adjusted.

20. The non-transitory computer readable medium of claim 19, wherein the synthetic image samples are associated with a congenital heart disease, the synthetic image samples including one or more of: magnetic resonance image data, echocardiography data, or computed tomography (CT) image data.

* * * * *